(12) United States Patent
Burns et al.

(10) Patent No.: US 7,005,050 B2
(45) Date of Patent: Feb. 28, 2006

(54) ELECTROPHORESIS IN MICROFABRICATED DEVICES USING PHOTOPOLYMERIZED POLYACRYLAMIDE GELS AND ELECTRODE-DEFINED SAMPLE INJECTION

(75) Inventors: Mark A. Burns, Ann Arbor, MI (US); Sundaresh N. Brahmasandra, Ann Arbor, MI (US); Victor M. Ugaz, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 10/277,348

(22) Filed: Oct. 22, 2002

(65) Prior Publication Data

US 2003/0116437 A1 Jun. 26, 2003

Related U.S. Application Data

(60) Provisional application No. 60/346,214, filed on Oct. 24, 2001.

(51) Int. Cl.
*G01N 27/447* (2006.01)
(52) U.S. Cl. .................................. 204/453; 204/251
(58) Field of Classification Search ................ 264/1.38; 204/451, 453, 455, 601, 604, 605, 470
See application file for complete search history.

(56) References Cited

U.S. PATENT DOCUMENTS

| | | | | |
|---|---|---|---|---|
| 5,503,722 A | * | 4/1996 | Guttman | 204/450 |
| 5,507,934 A | * | 4/1996 | Renfrew | 425/174 |
| 5,885,432 A | * | 3/1999 | Hooper et al. | 204/469 |
| 6,375,817 B1 | * | 4/2002 | Taylor et al. | 204/453 |

FOREIGN PATENT DOCUMENTS

JP 2001-083118 A * 3/2001

OTHER PUBLICATIONS

JPO machine translation of Hironobu et al. (JP 2001-083118 A).*
Page 5 of Electrophoresis: Theory, Techniques, and Biochemical and Clinical Applications, 2nd ed., Anthony Andrews, Clarendon Press-Oxford, 1986.*

* cited by examiner

*Primary Examiner*—Alex Noguerola
(74) *Attorney, Agent, or Firm*—Medlen & Carroll, LLP

(57) ABSTRACT

The present invention relates to a novel, small-scale, electrophoretic separation system based on photodefined polymers and electrode-defined sample injection. Diffusion and displacement coefficients may be modified by varying the gel concentration, the intensity of the incident UV radiation and the temperature at which the gel is run. The device is an major advance over current technology since it provides for a significant reduction in size of the micro-electrophoresis apparatus and a significant cost savings.

10 Claims, 16 Drawing Sheets

Photopolymerized gel in a complex device

F

Photopolymerized Gel Interface

E

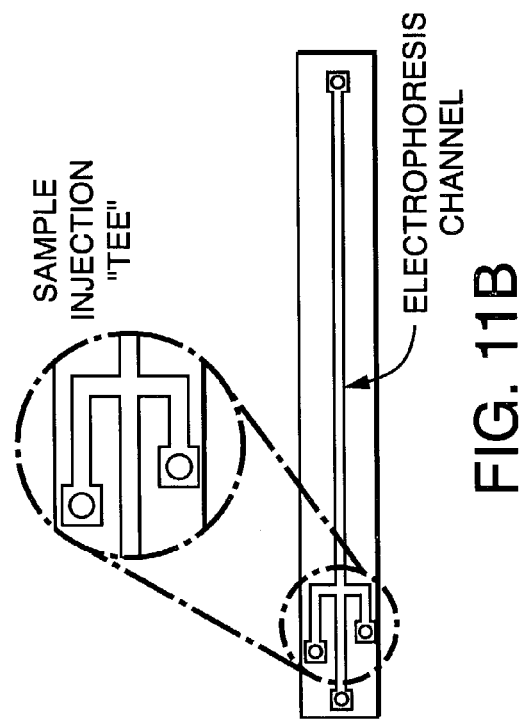
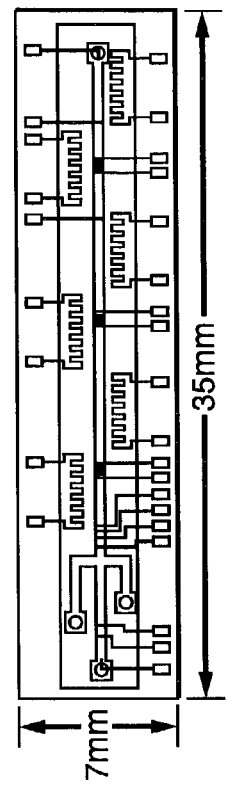
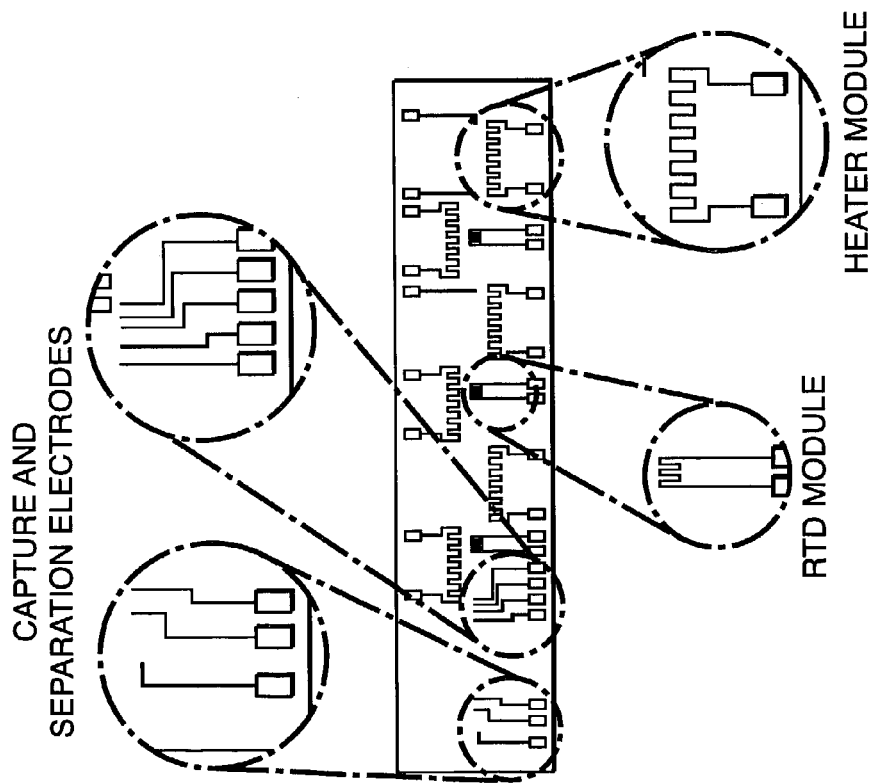
FIG. 11B
FIG. 11C
FIG. 11A

ELECTROPHORESIS IN MICROFABRICATED DEVICES USING PHOTOPOLYMERIZED POLYACRYLAMIDE GELS AND ELECTRODE-DEFINED SAMPLE INJECTION

This application for patent under 35 U.S.C. 111(a) claims priority to U.S. Provisional Application Ser. No. 60/346,214 filed on Oct. 24, 2001 under 35 U.S.C. 111(b).

This invention was made with funding from the National Institutes of Health; Grant Number 1 PO1 HG01984-01. The government may have certain rights in this invention.

FIELD OF THE INVENTION

The present invention relates to a novel, small-scale, electrophoretic separation system based on photodefined polymers (e.g., polyacrylamide gels) and electrode-defined sample injection giving superior resolution at a reduced cost and in less time.

BACKGROUND OF INVENTION

Despite the progress made towards the development of microfabricated DNA analysis systems, there are significant hurdles to the realization of small, portable DNA analysis systems. Although the cross sectional dimensions of typical microfabricated electrophoresis channels are on the order of those employed in conventional capillary systems, scale-down efforts have proven to be less than straightforward. Most of the miniaturized separation systems developed so far have adopted non-crosslinked polymer solutions as the medium of choice for DNA separations. The use of non-cross-linked sieving media necessitates the use of high electric fields to overcome the diffusion/dispersion of DNA fragments in these media and hinders the use of battery operation. In addition, most of these devices require external optical readers thereby increasing the cost substantially. While laser induced fluorescence provides detection of even single molecules, having a detection system orders of magnitude larger than the separation systems significantly diminishes the benefits of miniaturization (Woolley, A. T., et al., *Anal. Chem.* 70:684–688, 1998). Finally, high-resolution separations tend to require long separation lengths that result in devices with a relatively large footprint. These are some of the limitations that have restricted the applicability of microfabricated devices to laboratory based settings.

Unless DNA separations can be performed over much shorter length scales, it will be difficult to realize the enormous cost savings possible through mass production via photolithographic fabrication techniques. These techniques, routinely employed in the semiconductor industry, have the potential to allow tens or hundreds of devices to be produced on a single wafer. For example, once initial design costs have been paid, fabrication of an integrated DNA analysis device incorporating on-chip temperature control and fluorescence detection costs about $5000 per 25 wafers (Burns, M. A., et al., *Science* 282:484–487, 1998). If the separation length can be reduced to 0.5 cm, a yield of approximately 120 devices can be expected from a 10 cm wafer, resulting in a net cost just over $1.50 per device. This represents an incredible cost savings compared to macroscale DNA analysis systems, and becomes even more dramatic when combined with the essentially negligible reagent costs associated with the nanoliter sample volumes required.

Polyacrylamide gel electrophoresis (PAGE) offers the advantage of requiring significantly less power to achieve efficient separations over shorter separation lengths than separations in non-crosslinked media. These characteristics polyacrylamide gels make it an attractive choice for the development of a low-power, gel-preloaded, DNA analysis system. However, the use of polyacrylamide gels in microfabricated devices has been hindered by the same problems that have plagued traditional slab gel and capillary gel electrophoresis systems (Schmalzing, D. et al., *Electrophoresis* 20:3066–3077, 1999). Problems associated with in-situ preparation (lack of precise control over and knowledge of chemical properties and purity of the resulting product), short shelf life, operation and sample injection still need to be resolved. The in-situ polymerization of polyacrylamide also does not offer stringent control on the position, and shape of the resulting gel interface, which defines the shape of the injected sample. Localization of the separation matrix to a pre-defined section of the device is necessary for the development of integrated analysis systems incorporating sample preparation steps prior to the separation stage (Burns, M. A., et al., *Science* 282:484–487, 1998).

Along with the proper matrix composition and gel interface shape, the application of the sample to the gel interface is an important consideration. In all microfabricated separation systems, the process of loading the sample onto the separation matrix is extremely critical in determining the performance of these devices. Several sample injector designs have been used, most notably the cross injector (Jacobson, S. C., et al. *Anal. Chem.* 66:1107–1113, 1994; Fan, Z. H. and D. J., Harrison, *Anal. Chem.* 66:177–184, 1994; Manz, A., et al., *Trends Anal Chem.* 10:144–149, 1991) and the double-T injector (Manz, A., et al., *Trends Anal Chem.* 10:144–149, 1991; Effenhauser, C. S., et al., *Anal. Chem.* 65:2637–2642, 1993) design. While these sample injection schemes allow a sample plug of defined volume to be injected (typically 50–500 pL), no significant increase in sample concentration is achieved. Hence, reducing the size of the sample injection plug-width also reduces the amount of sample injected. Independent control of the amount of sample injected is difficult, necessitating the use of highly sensitive detectors to detect the separated fragments.

Electrokinetic focusing techniques have been modified and used to achieve an increase in sample concentration in microfabricated devices by introducing a mismatch between the sample buffer and a focusing buffer (Jacobson, S. C. and J. M. Ramsey, *Anal. Chem.* 69:3212–3217, 1997). Similarly, sample stacking has been achieved by positioning a porous membrane positioned immediately upstream of the gel interface (Khandurina, J., et al., *Anal. Chem.* 71:1815–1819, 1999). Unfortunately, both these techniques require electric potentials on the order of 1 to 2 kV to operate effectively. More recently, a sample compaction mechanism based on entropic trapping has been demonstrated (Han, J. and H. G. Craighead, *Science* 288:1026–1029, 2000). The DNA is trapped entropically in a well at low electric field strengths and can be released from the well as a well-defined plug by increasing the electric field strengths. However, this type of injection has currently been shown to work only for relatively large DNA molecules.

SUMMARY OF INVENTION

In one embodiment, the present invention relates to a novel, small-scale, electrophoretic separation system based on photodefined polymers (e.g., polyacrylamide gels) and electrode-defined sample injection giving superior resolution at a reduced cost and in less time.

In one embodiment, the present invention contemplates an ultra-short, integrated sample compaction and separation system using the techniques of the silicon microfabrication industry. Although the present invention is not limited to any particular mechanism, it is believed the use of photopolymerized polymer (e.g., polyacrylamide) sieving matrices overcomes many of the drawbacks of conventional polyacrylamide gel preparation. The present invention can reproducibly resolve a dsDNA standard of about 20 bp well into about the 500 bp range in just a few millimeters. The individual bands are clearly observed and appear essentially identical to a macro-scale electrophoresis separation. Since varying the polymer polymerization time strongly influences the structure and sieving properties of the polymerized polymer, a further potential advantage of the UV initiated chemistry of the present invention is the ability to tailor the pore structure of a single polymer by appropriate modulation of polymerization conditions.

In one embodiment, the present invention contemplates the use of microelectrodes. Although not limited to any particular mechanism, it is believed that the use of microelectrodes offers the ability to precisely define the shape and size of the injected sample plug by simple manipulation of the design of compaction electrode. Unlike standard electrokinetic injection schemes, almost an order of magnitude increase in the sample concentration can be achieved using the technique of the present invention with no additional broadening of the sample plug. The use of microelectrodes is not limited to low voltages and short injection distances. High voltages, especially with DC current, are also contemplated. Additionally, it is contemplated that adverse electrolytic effects, if any, can be minimized by using a permeation layer of agarose or acrylamide as is currently done in active DNA hybridization microchips (Heller, M., et al., *Electrophoresis* 21:157–164, 2000). Alternatively, microfabrication offers the possibility of depositing a bank of compaction electrodes with no change in process cost or complexity. Creative placement and activation of electrodes will result in far greater concentration enhancement.

Although the present invention is not limited to any particular mechanism or theory, it is believed that photodefined polymers (e.g., polyacrylamide gels) allow precise definition of the position and shape of the polymer (e.g., gel) interface with a microfabricated DNA analysis system. For example, the use of photodefined polyacrylamide gels is time and cost efficient, requires significantly shorter curing times than conventional chemically polymerized polyacrylamide gels, and offers the realization of high-resolution separations over short separation lengths. Further, the use of microelectrodes to define the size and shape of the injection plug allows extremely small but highly concentrated sample plugs to be generated. Microelectrode-based sample injection facilitates sample compaction (without migration) and independent control of both the amount of sample injected and the size of the sample plug.

In a preferred embodiment, the elements necessary for the construction of the electrophoresis devices and electrodes are microfabricated from silicon and glass substrates. Electronic components are fabricated on the same substrate material, allowing sensors and controlling circuitry to be incorporated in the same device. Since all of the components are made using conventional photolithographic techniques, multi-component devices can be readily assembled into complex, integrated systems.

It is not intended that the present invention be limited by the nature of the electrophoresis carried out in the microscale device. The electrophoresis includes, but are not limited to, the electrophoresis of nucleic acids, proteins, etc. Electrophoresis of nucleic acids include, but are not limited to sequencing, restriction enzyme digests, RFLP, detecting hybridization of nucleic acids and separation of amplified products (e.g., from PCR, strand displacement amplification (SDA), e.g., Beckton-Dickenson), etc. Electrophoresis of proteins include, but are not limited to mutation detection, sizing, presence or absence of a particular protein or proteins in a sample, etc. It is also not intended that the invention be limited by the particular purpose for carrying out electrophoresis. In one medical diagnostic application, for example, it may be desirable to differentiate between restriction digests to detect gene mutations. In another medical diagnostic application, it may be desirable to simply detect the presence or absence of specific peptides of pathogens in a clinical sample. For example, different species or subspecies of bacteria may have different susceptibilities to antibiotics; rapid identification of the specific species or subspecies present aids diagnosis and allows initiation of appropriate treatment.

In one embodiment, the polymerization of the gel is controlled by adjusting the intensity of the incident UV radiation. The UV radiation can be, for example, increased by moving the microdevice closer to the UV light source and decreasing the incident intensity by placing the microdevice under glass plates. Diffusion coefficients decrease slightly with increasing UV exposure level during polymerization. The same is true for dispersion coefficients, however, the change is more pronounced, especially at the lowest exposure level. Although the present invention is not limited by any particular theory, this trend is likely to be a manifestation of the complex interplay between reaction kinetics and gel pore morphology. It is notable that despite the limited range to which the incident UV intensity was varied, changes were still induced in the diffusion and dispersion characteristics of the gel. More pronounced changes in UV intensity will alter diffusion and dispersion even more dramatically.

In one embodiment, the gel structure can be altered by modifying the polymer concentration in the gel mix. In a preferred embodiment, the gel concentration is between about 4 and 15% (w/v). In a more preferred embodiment, the gel concentration is between about 6 and 12% (w/v). Although the present invention is not limited by any particular theory, it is believed that diffusion is decreased with increasing gel concentration. The effect is most pronounced between concentrations of about 9–12% (w/v).

In one embodiment, the effect of temperature exerts a strong influence on sieving performance and can be easily adjusted using integrated or external heaters. Although the present invention is not limited by any particular theory, it is believed that the magnitudes of the diffusion coefficients increase with increasing temperature. In a preferred embodiment, the maximum increase in the diffusion coefficient is between a temperature of about 50 and 60° C.

In one embodiment, the present invention contemplates a method for electrophoresis: (a) providing a microfabricated device comprising crosslinked polymer (e.g., polyacrylamide gel) and a sample; (b) depositing said sample on said polymer with a microelectrode and, (c) conveying said sample into said polymer to separate components of the sample in said polymer. It is not intended that the present invention be limited by the particular nature of the sample nor by the means of detecting the components of the sample after separation in the polymer.

The present invention contemplates a variety of silicon-based, micro-electrophoresis devices. In one embodiment, the device comprises: i) a housing comprised of silicon, ii) an electrophoresis channel or channels etched in said silicon, iii) a polymer (e.g., a crosslined polyacrylamide gel) deposited into said channels, and iv) a microelectrode sample injection means. In one embodiment, the device is assembled in two parts. First, the channels are etched in any number of configurations. Secondly, this piece is bonded with a silicon-based chip containing the electronics. This allows for both customization (in the first piece) and standardization (in the second piece). After assembly the polymer is deposited into the channels.

In one embodiment, the present invention also contemplates micro-electrophoresis devices made from glass or plastic substrates. Such devices may be etched or molded. The present invention also contemplates micro-electrophoresis devices made from moldable polymers such as poly(dimethylsiloxane) (PDMS) and poly(methylmethaceylate) (PMMA).

In one embodiment, the present invention contemplates a method comprising: (a) providing (i) a microfabricated device comprising a polymer (e.g., polyacrylamide gel), (ii) a microelectrode and, (iii) a sample; (b) depositing said sample on said polymer with a microelectrode and, (c) conveying said sample in said polymer to separate components of said sample in said polymer. In another embodiment, the polymer is crosslinked. In yet another embodiment, the polymer is not crosslinked. In still yet another embodiment, non-crosslinked linear polymers (i.e., linear polyacrylamide and non-polyacrylamide gels) are used. Although embodiments of the present invention are not limited to any particular linear polymer, examples are poly (2-hydroxyethyl methacrylate), Poly(lactic acid)-poly(ethylene glycol) and poly-N,N-dimethylacrylamide.

In one embodiment, the present invention also contemplates that the polymer (e.g., polyacrylamide gel) is photopolymerized. The present invention additionally contemplates that the photopolymerization comprises exposing said polymer to light such as UV irradiation. It is not intended that the present invention be limited to particular light sources or restricted to only certain wavelengths or exposure times. Nonetheless, in a preferred embodiment the light source is a Reproset™ UV gel box (Amersham) and the UV light is UVA from a 40 watt mercury vapor bulb with cure times of 6–7 minutes (ReproGel™ High Resolution) or 8–10 minutes (ReproGel™ Long Read) produced optimal results.

The one embodiment of the present invention provides the use of microelectrodes to concentrate the sample: (a) providing (i) first and second electrodes, (ii) a microelectrophoresis device and (iii) a sample, (b) applying the sample to the microelectrophoresis device, (c) applying an electric current to said first and second electrodes where said first electrode has a negative charge and said second electrode has a positive charge until at least 90% of the sample has accumulated at said second electrode. It is preferred that said first and second electrodes are positioned such that the second electrode is at about the surface of the polymer (e.g., gel) and the first electrode is positioned in the loading channel about 250 to 1600 microns from the second electrode.

The one embodiment of the present invention provides the use of microelectrodes to concentrate the sample: (a) providing (i) first, second and third electrodes, (ii) a microelectrophoresis device and (iii) a sample, (b) applying the sample to the microelectrophoresis device, (c) applying an electric current to said first and second electrodes where said first electrode has a negative charge and said second electrode has a positive charge until at least 90% of the sample has accumulated at said second electrode and, (d) applying electric current to said second and said third electrodes where said second electrode has a negative charge and said third electrode has a positive charge until the sample has become concentrated. It is preferred that said first and second electrodes are positioned such that the second electrode is at about the surface of the polymer (e.g., gel) and the first electrode is positioned in the loading channel about 250 to 1600 microns from the second electrode.

In one embodiment, the present invention contemplates that the amount of sample collected is defined by the electric field strength and time of sample compaction. The present invention also contemplates the size and shape of the sample plug is defined by the size and shape of the electrode. Although sample plugs are not limited to a particular size, in one embodiment, sample plug widths of 50 microns or less are contemplated. The present invention further contemplates that the width of the sample plug will be further reduced as a consequence of additional compaction at the polymer interface after the sample is run into the polymer. Hence, it is contemplated that the novel loading scheme of the present invention both increases the concentration of the sample to be separated and significantly reduces degradation in separation resolution due to the size of the injected sample plug, a quantity of increased relative importance in ultra-short systems.

In one embodiment, the present invention contemplates a device, comprising: i) a housing; ii) one or more electrophoresis channels etched into said housing; and iii) a microelectrode sample injection component configured to inject one or more samples into said channels. In another embodiment, the present invention contemplates the device wherein a polymer (e.g., a crosslinked gel) is deposited in said one or more channels. In yet another embodiment, the present invention contemplates the device wherein said crosslinked gel is a polyacrylamide gel. In yet another embodiment, the present invention contemplates the polymer being a non-crosslinked gel (e.g., non-crosslinked polyacrylamide gel). In still yet another embodiment, the present invention contemplates linear polymers (e.g., linear polyacrylamide, poly (2-hydroxyethyl methacrylate), Poly(lactic acid)-poly(ethylene glycol) and poly-N,N-dimethylacrylamide). In still yet another embodiment, the present invention contemplates the device wherein said polyacrylamide gel is photopolymerized. In still yet another embodiment, the present invention contemplates the device wherein said housing comprises glass, silicon or plastic.

In one embodiment, the present invention contemplates a device, comprising: i) a housing; ii) one or more electrophoresis channels etched into said housing; iii) a polymer deposited in said one or more channels; and iv) a microelectrode sample injection component configured to inject one or more samples into said polymer. In another embodiment, the present invention contemplates the device wherein said polymer is crosslinked polyacrylamide gel. In yet another embodiment, the present invention contemplates the polymer being a non-crosslinked gel (e.g., non-crosslinked polyacrylamide gel). In still yet another embodiment, the present invention contemplates linear polymers (e.g., linear polyacrylamide, poly(2-hydroxyethyl methacrylate), Poly (lactic acid)-poly(ethylene glycol) and poly-N,N-dimethylacrylamide). In still yet another embodiment, the present invention contemplates the device wherein said polymer is photopolymerized. In still yet another embodiment, the present invention contemplates the device wherein said housing comprises glass, silicon or plastic.

In one embodiment, the present invention contemplates a method, comprising: a) providing a sample and a device, wherein said device comprises i) a housing; ii) one or more electrophoresis channels etched into said housing; iii) a polymer deposited in said one or more channels; and iv) a microelectrode sample injection component configured to inject one or more samples into said polymer; and b) injecting said sample into said polymer with said microelectrode sample injection component. In another embodiment, the present invention contemplates the device wherein said polymer is crosslinked polyacrylamide gel. In yet another embodiment, the present invention contemplates the polymer being a non-crosslinked gel (e.g., non-crosslinked polyacrylamide gel). In still yet another embodiment, the present invention contemplates linear polymers (e.g., linear polyacrylamide, poly(2-hydroxyethyl methacrylate), Poly(lactic acid)-poly(ethylene glycol) and poly-N,N-dimethylacrylamide). In still yet another embodiment, the present invention contemplates the device wherein said polymer is photopolymerized. In still yet another embodiment, the present invention contemplates the device wherein said housing comprises glass, silicon or plastic.

In one embodiment, the present invention contemplates a methods for sample compaction. For example, samples are compacted between an approximately 50 $\mu$m thin electrode (anode) and an approximately 50 $\mu$m thin electrode (cathode) (i.e., electric field strength). It is further contemplated that the distance between the two electrodes defines both the total sample available for the compaction, and the electric field between the two electrodes. For example, a voltage of 2.0 V applied between two electrodes separated by approximately 250–1600 $\mu$m results in electric field strengths of ~12–80 V/cm.

One embodiment of the present invention also contemplates, locating a bank of compaction electrodes in the electrophoresis device of the present invention. The bank of electrodes comprises two or more electrodes. The electrodes are located in the loading channel, at the surface of the polymer and within the polymer. Although not limited to any particular theory, it is believed that creative placement and activation of electrodes will result in far greater concentration enhancement.

In one embodiment, the present invention also contemplates a photodefined polymer. Although the present invention is not limited to any particular method, in one embodiment, the unpolymerized polymer is partly shaded on the end wherein the samples will be loaded. The polymer is then exposed to UV illumination. The unshaded portion of the polymer will polymerize while the shaded portion will remain unpolymerized. Removal of the polymerized portion will leave a well defined sample loading surface.

In one embodiment, the present invention also contemplates that the housing is composed from a substance selected from a group consisting of silicon, glass and plastic. The present invention additionally contemplates that the plastic is selected from a group consisting of poly(dimethylsiloxane) (PDMS) and poly(methylmethaceylate) (PMMA).

The present invention contemplates, in one embodiment, a method comprising: (a) providing; (i) a microelectrophoresis device comprising a polymer deposited in a loading channel; (ii) first and second microelectrodes wherein said second microelectrode is located approximately at the surface of said polyacrylamide gel said first microelectrode is located approximately in said loading channel; and (iii) a sample; (b) introducing the sample to said loading channel to produce a loaded channel; (c) applying a negative charge to said first microelectrode and applying a positive charge to said second microelectrode to concentrate said sample at said second microelectrode. In another embodiment, the present invention contemplates the method, wherein said first electrode is located 250 to 1600 $\mu$m from said second electrode. In yet another embodiment, the present invention contemplates that the polymer is a crosslinked gel. In still yet another embodiment, the present invention contemplates the polymer is deposited in said one or more loading channels. In still yet another embodiment, the present invention contemplates the loading channel comprises glass, silicon or plastic.

The present invention contemplates the method in the above paragraph, wherein the diffusion and displacement coefficients of said polymer are controlled by varying the intensity of the incident the UV radiation. The present invention also contemplates the method in the above paragraph, wherein said polymer has a concentration between about 2 and 15% (w/v). The present invention contemplates further that in the method in the above paragraph the sieving performance of said polymer is controlled by the temperature of said polymer at the time said negative and positive charges are applied to said first and second electrodes.

Definitions

The following definitions are provided for the terms used herein:

"Biological reactions" means reactions involving biomolecules such as enzymes (e.g., polymerases, nucleases, etc.) and nucleic acids (both RNA and DNA). Biological samples are those containing biomolecules, such proteins, lipids, nucleic acids. The sample may be from a microorganism (e.g., bacterial culture) or from an animal, including humans (e.g. blood, urine, etc.). Alternatively, the sample may have been subject to purification (e.g. extraction) or other treatment. Biological reactions require some degree of biocompatability with the device. That is to say, the reactions ideally should not be substantially inhibited by the characteristics or nature of the device components.

"Chemical reactions" means reactions involving chemical reactants, such as inorganic compounds.

"Channels" are pathways through a medium (e.g., silicon) that allow for movement of liquids and gasses. Channels thus can connect other components, i.e., keep components "in liquid communication." "Microdroplet transport channels" are channels configured (in microns) so as to accommodate "microdroplets". While it is not intended that the present invention be limited by precise dimensions of the channels or precise volumes for microdroplets, illustrative ranges for channels and microdroplets are as follows: the channels can be between 0.35 and 50 $\mu$m in depth (preferably 20 $\mu$m) and between 50 and 1000 $\mu$m in width (preferably 500 $\mu$m), and the volume of the microdroplets can range (calculated from their lengths) between approximately one (1) and (100) nanoliters (more typically between ten and fifty). An "electrophoresis channel" is a channel substantially filled with a material that aids in the differential migration of DNA.

"Conveying" means "causing to be moved through" as in the case where a microdroplet is conveyed through a transport channel to a particular point, such as a reaction region. Conveying can be accomplished via flow-directing means.

"Flow-directing means" is any means by which movement of a microdroplet in a particular direction is achieved. A preferred directing means employs a surface-tensiongradient mechanism in which discrete droplets are differentially heated and propelled through etched channels.

"Hydrophilicity-enhancing compounds" are those compounds or preparations that enhance the hydrophilicity of a component, such as the hydrophilicity of a transport channel. The definition is functional, rather than structural. For example, Rain-X™ anti-fog is a commercially available reagent containing glycols and siloxanes in ethyl alcohol. However, the fact that it renders a glass or silicon surface more hydrophilic is more important than the reagent's particular formula.

"Initiating a reaction" means causing a reaction to take place. Reactions can be initiated by any means (e.g., heat, mixing of reagents, wavelengths of light, addition of a catalyst, etc.)

"Liquid barrier" or "moisture barrier" is any structure or treatment process on existing structures that prevents short circuits and/or damage to electronic elements (e.g., prevents the destruction of the aluminum heating elements). In one embodiment of the present invention, the liquid barrier comprises a first silicon oxide layer, a silicon nitride layer, and a second silicon oxide layer.

"Merging" is distinct from "mixing". When a first and second microdroplet is merged to create a merged microdroplet, the liquid may or may not be mixed. Moreover, the degree of mixing in a merged microdroplet can be enhanced by a variety of techniques contemplated by the present invention, including by not limited to reversing the flow direction of the merged microdroplet.

"Nucleic Acid Amplification" involves increasing the concentration of nucleic acid, and in particular, the concentration of a particular piece of nucleic acid. A preferred technique is known as the "polymerase chain reaction." Mullis, et al., U.S. Pat. Nos. 4,683,195 and 4,683,202, hereby incorporated by reference, describe a method for increasing the concentration of a segment of target sequence in a mixture of genomic DNA without cloning or purification. This process for amplifying the target sequence consists of introducing a molar excess of two oligonucleotide primers to the DNA mixture containing the desired target sequence. The two primers are complementary to their respective strands of the double-stranded sequence. The mixture is denatured and then allowed to hybridize. Following hybridization, the primers are extended with polymerase so as to form complementary strands. The steps of denaturation, hybridization, and polymerase extension can be repeated as often as needed to obtain are relatively high concentration of a segment of the desired target sequence. The length of the segment of the desired target sequence is determined by the relative positions of the primers with respect to each other, and therefore, this length is a controllable parameter. By virtue of the repeating aspect of the process, the method is referred to by the inventors as the "Polymerase Chain Reaction" (hereinafter PCR). Because the desired segment of the target sequence become the dominant sequences (in terms of concentration) in the mixture, they are said to be "PCR-amplified."

"Microfabricated", "micromachined" and "micromanufactured" mean to build, construct, assemble or create a device on a small scale (e.g., where components have micron size dimensions). In one embodiment, electrophoresis devices are microfabricated ("microfabricated electrophoresis device") in about the millimeter to centimeter size range.

"Microelectrode" means an electrode that was microfabricated on a small scale. In the context of the present invention, the microelectrode is small enough to load samples onto the microfabricated electrophoresis device of the present invention. For example, in one embodiment, the microelectrode of the present invention was fabricated by first depositing a 2000 Å thick layer of thermal oxide on the silicon wafer to provide electrical insulation. A positive photoresist (PR 1827, Hoechst Celanese) was applied, patterned and developed. A 300 Å thick titanium metal layer followed by a 2000 Å thick platinum metal layer was deposited on the substrate by electron beam evaporation. The resist and the overlying metal layers were then 'lifted off' by development using Microposit 1112A remover in solution (Shipley Co., Newton, Mass.). The wafers were then rinsed and dried. Microelectrodes may also be deposited on quartz and glass wafers using a similar process.

"Polyacrylamide (gel)" is a term understood by those practiced in the art to mean a gel that suppresses convective mixing of the fluid phase through which electrophoresis takes place and contributes molecular sieving. Polyacrylamide gels may be crosslinked or non-crosslinked.

"Crosslinked" means the linking of the chains of a polymer (e.g., polyacrylamide) to one another so that the polymer, as a network, becomes stronger and more resistant to being dissolved and permits better separation of sample components when used in electrophoresis. Bis-acrylamide is an example of a cross-linking agent used in polyacrylamide electrophoresis.

"Polymer" refers to a substance formed from two or more molecules of the same substance. Examples of a polymer are gels, crosslinked gels and polyacrylamide gels. Polymers may also be linear polymers. In a linear polymer the molecules align predominately in chains parallel or nearly parallel to each other. In a non-linear polymer the parallel alignment of molecules is not required.

"Sample injection means", "microelectrode sample injection means" or "microelectrode sample injection component" refer to the method or device used to load sample onto a polyacrylamide gel, e.g., by inserting the sample into the loading chamber and applying electric current in order to compact the sample. Details of the procedure are in Example 5.. In the present invention the sample injection means is performed, e.g., using a microelectrode.

"Photodefined polyacrylamide gels" are polyacrylamide gels that are polymerized by exposure of at least a part of the gel to a light source. The unexposed part of the gel may then be removed (e.g., by washing) leaving a well defined sample loading surface.

"Injection plug" and "sample plug" refer to the sample deposited on the gel and concentrated by microelectrodes.

"Concentration," "concentrated" and "to concentrate a sample" and similar terms refer to the increase in density or packing of solutes in a sample by removing part of the liquid in the sample. For example, the electrophoresis samples of the embodiments of the present invention are concentrated by bringing together the solutes of the sample at an electrode and displacing the water or other liquids at the electrode until the sample is concentrated to about 50 microns or less.

"Micro-electrophoresis device" refers to a small (e.g., micron size components) scale device for performing electrophoresis. In one embodiment, it is contemplated that the micro-electrophoresis device comprises electrophoresis channels of about 400 $\mu$m or less (width) by 40 $\mu$m or less (depth).

"UV illumination" and "UV irradiation" shall refer to UVA illumination. In one embodiment of the present invention, the UVA illumination is from an "UVA illumination source", e.g., an Amersham ReproSet™ UV gel set box using a 40 watt mercury vapor bulb.

"Loading channel" refers to a channel in the electrophoresis device of embodiments of the present invention, wherein the gel and samples of the present invention are deposited.

"Shielding device" refers to a device designed to sheild a portion of the gel from UVA illumination during photopolymerization.

DESCRIPTION OF THE FIGURES

FIG. 11 (A) shows a schematic depicting the electrode, heater and RTD array on the silicon substrate; (B) the electrophoresis channel layout on the glass substrate; and (C) the assembled device consisting of the glass channel bounded on top of the silicon substrate.

GENERAL DESCRIPTION OF INVENTION

Figure 1C:
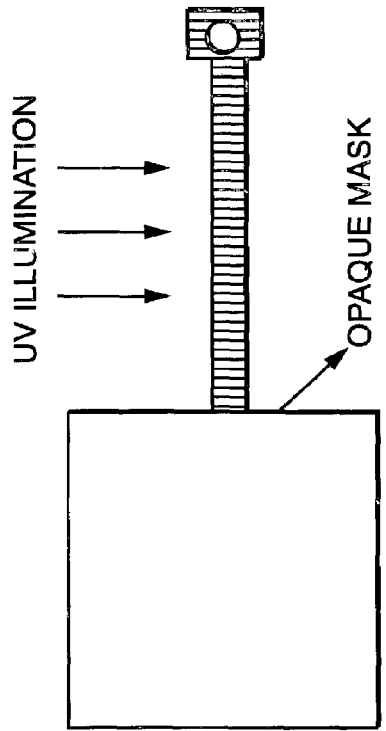
FIGS. 1a, 1b, 1c, 1d, 1e and 1f illustrate the masking process used to position the polyacrylamide gel within the separation channel of a microfabricated electrophoresis device. (a) Empty separation channel, (b) channel filled with monomer/crosslinker mixture, (c) channel sections masked for polymerization, (d) final polymerized gel, (e) photograph of typical gel interface (arrow denoted gel interface), (f) Localization of gel interface in a complex microchannel network.
Figure 1D:
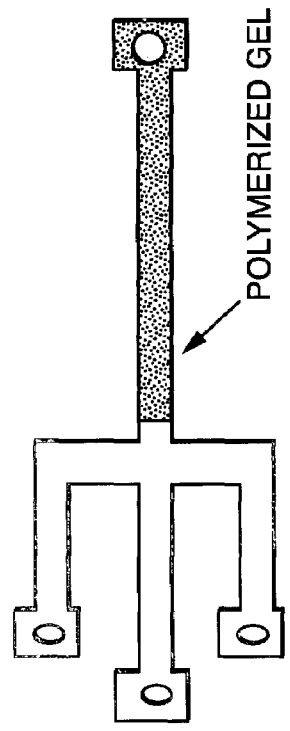
Figure 1A:
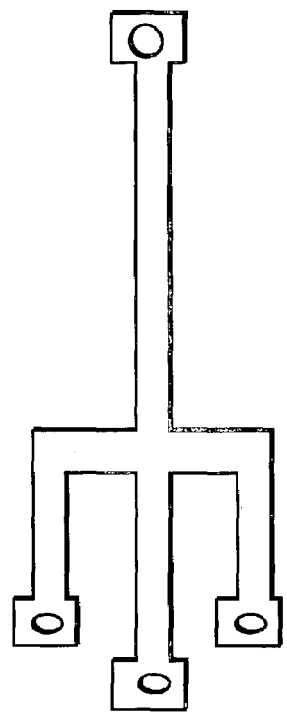
Figure 1B:
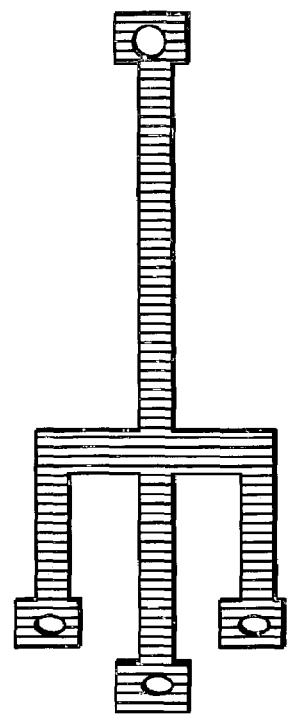
Figure 1:
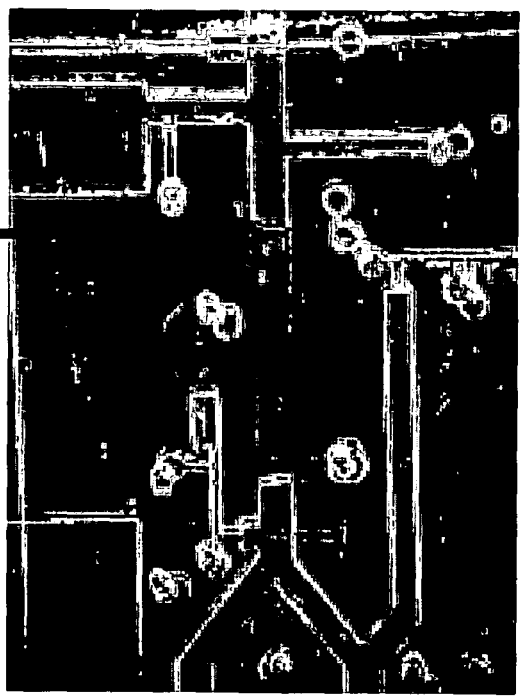
Figure 1:
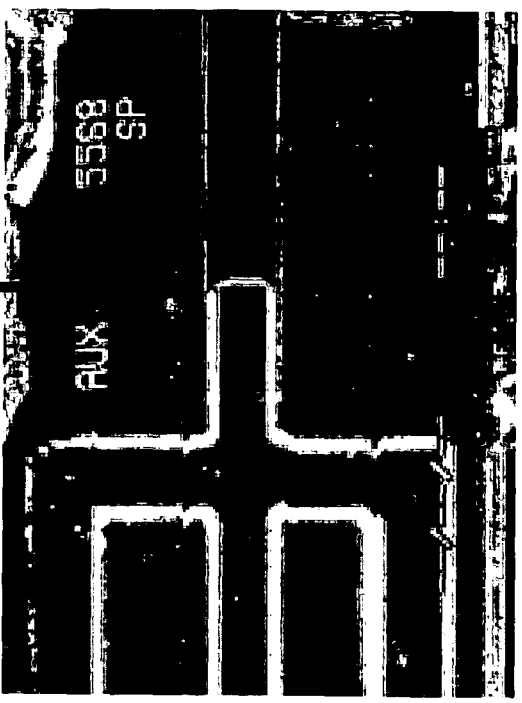
Figure 2:
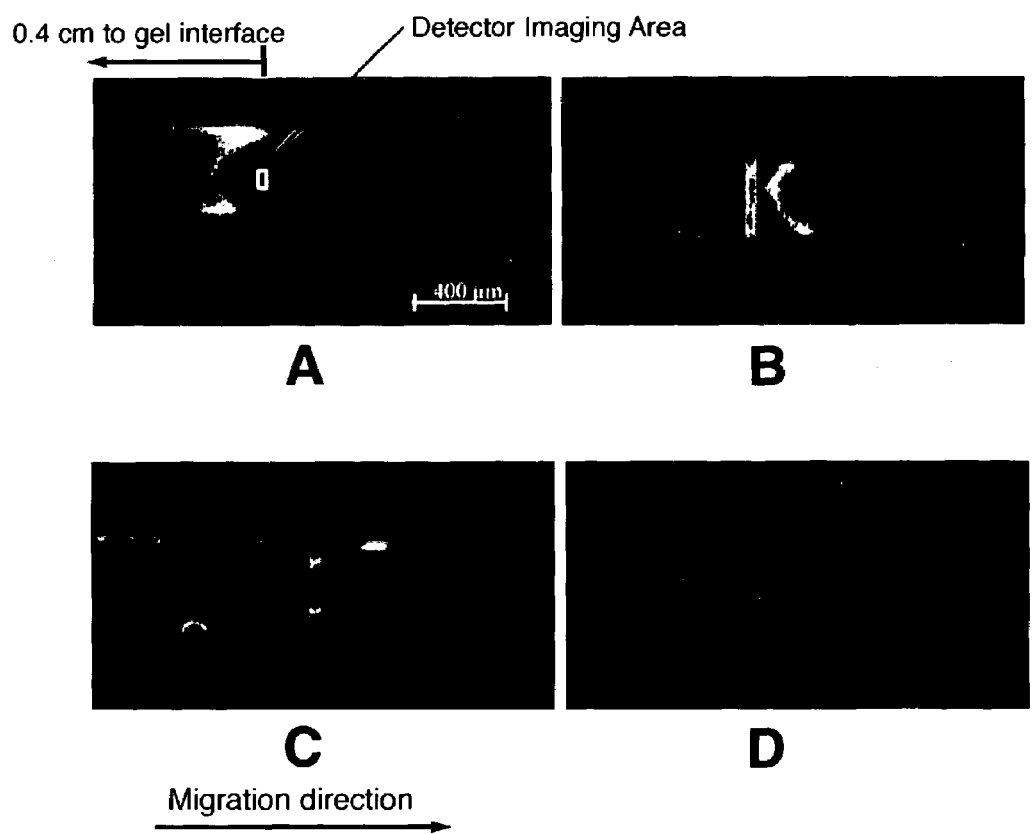
FIG. 2 shows a video sequence depicting the influence of gel polymerization time on separation performance of a 20 base pair (bp) ladder under native gel conditions using ReproGel High Resolution.

Upon completion of the Human Genome Project (HGP), a continuing effort of the human genetics research community will be the examination of differences within populations and of individual variants from the defined archetype. Current DNA genotyping technologies are adequate for the detailed analysis of samples that range in number from hundreds to thousands per year. Genotyping projects on the order of millions of assays, however, are beyond the capabilities of today's laboratories because of the current inefficiencies in (i) liquid handling of reagent and DNA template solutions, (ii) measurement of solution volumes, (iii) mixing of reagent and template, (iv) controlled thermal reaction of the mixed solutions, (v) sample loading onto an electrophoresis gel and (vi) DNA product detection on size-separating gels.

The present invention provides methods to greatly improve items (v) and (vi) above, sample loading onto an electrophoresis gel and DNA product detection on size-separation gels.

The description of the invention below involves: I) Overview; II) Microfabrication techniques for manufacture of silicon-based devices; III) Component design (particularly the electrophoresis module and the radiation detectors); IV) Photopolymerized polyacrylamide gels; and V) Design of electrodes.

I. Overview

Microfabrication techniques are viewed as the answer to the daunting problem of sequencing large amounts of DNA economically. Microfabricated channels offer a radically different platform to perform capillary electrophoretic separations. When applied to DNA electrophoresis, such devices consist of microfabricated channels in which the electrophoresis and detection of these fragments occur. The small size of these microchannels allow a large number of channels to be placed together generating more electrophoretic lanes per unit (Carrilho, E., Electrophoresis 21:55–65, 2000). The planar structure also facilitates superior detection using either optical imaging or scanning lenses (Schmalzing, D. et al., Electrophoresis 20:3066–3077, 1999). Microfabricated devices also offer significant control over the size of the injected sample plug, resulting in shorter separation lengths and faster separations. Finally, from a manufacturing standpoint, the batch fabrication techniques of microfabrication allows the cost per device to decrease dramatically with the size of the device. The cost of such devices could be further reduced by using inexpensive plastic substrates. Microchips used for electrophoresis have been fabricated either using conventional photolithography on glass, silicon or plastic substrates (Jacobson, S. C., et al. *Anal. Chem.* 66:1107–1113, 1994), or by molding polymers such as poly(dimethylsiloxane) (PDMS) (Effenhauser, C. S., et al., *Anal. Chem.* 69:3451–3457, 1997; Duffy, D. C., et al., *Anal. Chem.* 70:4974–4984, 1998) and poly(methylmethacrylate) (PMMA) (Ford, S. M., et al., *Microcol.* 10:413–422, 1998). Several research groups have reported analysis of various types of DNA fragments, including oligonucleotides (Effenhauser, C. S., et al., *Anal. Chem.* 66:2949–2953, 1994), restriction fragments (Woolley, A. T. and R. A. Mathies, *Proc. Natl. Acad. Sci, USA* 91:11348–11352, 1994), PCR products (Woolley, et al.,*Anal. Chem.* 67:3676–3680, 1995), sequencing mixtures (Woolley, A. T. and R. A. Mathies, *Anal. Chem.* 67:3676–3680, 1995) and short tandem repeats (Schmalzing, D., et al., *Proc. Natl. Scad. Sci, USA* 94:684–688, 1998) using a variety of polymeric sieving media. However, these prior art techniques leave much to be desired in that gel resolution is non-optimal and the procedures and equipment are not economical to procure and use. The present invention contemplates a novel system based on photodefined, crosslinked polyacrylamide gels and electrode-defined sample injection that gives superior gel resolution at a reduced cost and in less time.

II. Microfabrication Of Silicon-Based Devices

As noted previously, silicon has well-known fabrication characteristics and associated photographic reproduction techniques. The principal modem method for fabricating semiconductor integrated circuits is the so-called planar process. The planar process relies on the unique characteristics of silicon and comprises a complex sequence of manufacturing steps involving deposition, oxidation, photolithography, diffusion and/or ion implantation, and metallization, to fabricate a "layered" integrated circuit device in a silicon substrate. See, e.g., W. Miller, U.S. Pat. No. 5,091,328, hereby incorporated by reference.

For example, oxidation of a crystalline silicon substrate results in the formation of a layer of silicon dioxide on the substrate surface. Photolithography can then be used to selectively pattern and etch the silicon dioxide layer to expose a portion of the underlying substrate. These openings in the silicon dioxide layer allow for the introduction ("doping") of ions ("dopant") into defined areas of the underlying silicon. The silicon dioxide acts as a mask; that is, doping only occurs where there are openings. Careful control of the doping process and of the type of dopant allows for the creation of localized areas of different electrical resistivity in the silicon. The particular placement of acceptor ion-doped (positive free hole, "p") regions and donor ion-doped (negative free electron, "n") regions in large part defines the interrelated design of the transistors, resistors, capacitors and other circuit elements on the silicon wafer. Electrical interconnection and contact to the various p or n regions that make up the integrated circuit is made by a deposition of a thin film of conductive material, usually aluminum or polysilicon, thereby finalizing the design of the integrated circuit.

Of course, the particular fabrication process and sequence used will depend on the desired characteristics of the device. Today, one can choose from among a wide variety of devices and circuits to implement a desired digital or analog logic feature.

In a preferred embodiment, the microfabricated devices comprise an etched glass channel network bonded to a silicon/quartz substrate containing the microelectrodes. Fabrication of the microelectrodes is accomplished by first depositing a 2000 Å thick layer of thermal oxide on the silicon wafer to provide electrical insulation. A positive photoresist (PR 1827, Hoechst Celanese) is applied, patterned and developed. A 300 Å thick titanium metal layer followed by a 2000 Å thick platinum metal layer is deposited on the substrate by electron beam evaporation. The resist and the overlying metal layers are then 'lifted off' by development using Microposit 1112A remover in solution (Shipley Co., Newton, Mass.). The wafers are then rinsed and dried. Microelectrodes have also been deposited on quartz and glass wafers using a similar process. The initial step of growing a thermal oxide is not necessary for glass/quartz substrates.

Channels are fabricated by depositing 600 Å chromium metal layer followed by a 4000 Å thick layer of gold on the surface of a 500 $\mu$m thick glass (Dow Corning Pyrex 7740, 100 mm diameter). A 0.06 $\mu$m layer of chromium is used as the adhesion layer. Photoresist (PR 1827, Hoechst Celanese) is applied and patterned using a channel mask and developed. The metal layers are etched in a commercial gold etchant (Gold Etchant TFA, Transene Co., Danvers, Mass.) and chromium etchant (CR-14, Cyantek Inc., Fremont, Calif.). The accessible glass is then etched in a freshly prepared solution of hydrofluoric and nitric acid (7:3 v/v). The rate of etching is about 8 $\mu$m/min and the etch-depth was measured using a surface profilometer. After etching to the desired depth, the metal layers are removed using the respective etchants, and the wafer is rinsed in DI (deionized) water, air dried and oven-dried at 100° C. for 20 minutes. The final channel dimensions are approximately 400 $\mu$m (width) and 40 $\mu$m (depth).

Holes (~0.15 mm radius) are drilled from the top of the glass surface to access the microchannels on the bottom surface of the glass wafer by electrochemical discharge drilling (Shoji, S. and M. Esashi, *Tech. Digest of the 9th Sensor Symp.* 27–30, 1990). The individual devices on the glass and silicon wafers are then diced and bonded using optical adhesive (SK-9 Lens Bond, Summers Laboratories, Fort Washington, Pa.). The bond was cured under a UV light source (365 nm) for 24 hours. Finally, the assembled devices are wired to printed circuit boards and fitted with silicone electrophoresis buffer wells.

III. Component Design

The present invention contemplates one or more gel electrophoresis modules as a component of the microscale device. Theoretical and empirical research has indicated that reducing the thickness of the electrophoresis channel leads to improved resolution. Thinner gels dissipate heat more readily and allow higher voltages to be used, with concomitant improvements in separation. The position and width of the electrophoresis detector are also important to the ultimate resolution of the electrophoresis system. A micromachined electronic detector, such as a photodiode, placed in the underlying silicon substrate can be less than one micron from the gel matrix and can have a width of 5 microns or less. Since the gel length required for the resolution of two migrating bands is proportional to the resolution of the detector, the incorporation of micron-width electronic detectors can reduce the total gel length required for standard genotyping by at least an order of magnitude.

To demonstrate that standard gel electrophoresis can operate in micron-diameter channels, modules were fabricated using etched glass channels and fluorescent-labeled DNA (YOYO intercalating dye). Polyacrylamide gel electrophoresis of a complex DNA mixture was performed in a channel 500 µm wide and 20 µm deep. The electrophoresis was performed with the positive electrode to the right and the DNA sample applied at the left. The white vertical line is the gel-to-buffer interface. The DNA sample (BluescriptKS digested with MspI) is labeled with intercalating UV-fluorescent dye (YOYO-1) and is visualized under incandescent light. Separation of the component bands is clearly visible less than 300 µm from the buffer reservoir-to-gel interface. The high resolution of the detector (in this case, a microscope) allowed the use of an unusually short gel, resolving several closely eluting bands.

The present invention contemplates an electrophoresis unit that integrates a micromachined channel and an electronic DNA detector. The channel is constructed using a sacrificial etch process on a single silicon wafer rather than the bonded surface-etch method described earlier. In the sacrificial etch technique, the channel configuration is patterned by depositing on the wafer surface an etch-sensitive material (phosphosilicate glass, $SiO_2.P_x$) with a thickness equivalent to the desired channel height. A triple-layer overlay of plasma-enhanced chemical vapor deposited silicon nitride, undoped polycrystalline silicon, and silicon nitride ($Si_xN_y/polySi/Si_xN_y$) completely covers the sacrificial material with the exception of small access holes on the top or sides. A selective liquid etch removes the sacrificial layer material, but not the overlay or the underlying substrate. The sacrificial etch technique results in a complete channel being formed directly on the substrate containing the electronic components. The 3 µm deep channel has two buffer reservoirs on either end with integral phosphorus-doped polycrystalline silicon electrodes. The channel height formed by this technique (~3 µm) is considerably smaller than the height of the bonded structures due to the limitations of the sacrificial layer deposition and the strength of the overlying layer. Note that, for these channel dimensions, liquid drops would have volumes on the order of picoliters.

While fluorescent detection is preferred (see below) detection or radioactivity is also contemplated in connection with photopolymerized gels. A radiation detector, consisting of a 10 µm wide "p-n"-type diode with a 5 µm wide guard ring around the outer edge, is fashioned directly into the silicon substrate underneath the channel. In this implementation, an integral radiation detector was chosen because of (i) high sensitivity (a single decay event), (ii) small aperture dimensions, and (iii) well-know fabrication and response characteristics. On this electrophoresis system, a 1 cm long, 3 µm thick gel is able to perform as separation on a 80 and a 300 base-pair fragment of DNA. It should be noted that this diode, although currently configured for high-energy beta particle detection, can also operate as a photon detector. With proper wavelength filters and light sources, detection of fluorescence emission may be accommodated with a similar device.

Radiation detectors were prepared as follows. A 200½-cm, (100), float zone, boron-doped, p-type silicon wafer was used as a substrate. Diffused layers of phosphorus ($5\times10^{14}$ $cm^{-2}$) and boron ($1\times10^{15}$ $cm^{-2}$) were ion-implanted onto the sample in lithographically-defined regions; thermal silicon oxide was grown (0.2 µm at 900° C.) over the wafer; and contact holes were etched to the diffusion layer using buffered hydrofluoric acid solution (5:1). A 3.3 µm layer of Microposit 1400-37 photoresist was patterned to define the metal pads; 50 nm chromium followed by 400 nm gold was evaporated over the resist; and the metallization lifted off the regions retaining the resist. A layer of Microposit 1813 photoresist was applied across the wafer and baked for 110° C. for 30 minutes to form an aqueous solution barrier. Radioactive phosphorus ($^{32}P$) decay events could be detected using a sample of labeled DNA in PCR reaction buffer placed on the photoresist layer. The detector was connected to a charge-sensitive preamplifier (EV-Products 550A), followed by a linear shaping amplifier and a standard oscilloscope. Output was from the radiation detector collected on an oscilloscope trace and showed individual decay events from $^{32}P$-labeled DNA. The aqueous DNA sample was placed directly on the detector and sampled for 30 seconds.

IV. Photopolymerized Polyacrylamide Gels

One of the chief drawbacks of the use of polyacrylamide gels in high-throughput applications is the necessity of casting a new gel prior to each electrophoresis run, a process typically requiring up to an hour to complete using standard polymerization chemistries. Recently developed photo-initiated gels greatly speed this process by substituting UV-activated initiators for the standard chemical initiators in the polymerization mixture. Consequently, polymerization times can be reduced to 5–10 minutes, on the order of the time required to load a capillary with a linear polyacrylamide matrix. In situ gel polymerization also alleviates the difficulties associated with loading externally polymerized separation matrices into capillary-sized channels; the monomer solution for the gels is approximately the same viscosity as water and spontaneously wicks into the separation channel.

A further, and thus far unexplored, benefit of the UV-initiated chemistry is that the polymerization reaction can be localized at a specific region within a microfabricated device by selectively illuminating the channel, or portions of the channel, where the gel is to be located. This ability to precisely position the gel with a well-defined flat interface confers a further advantage over linear polyacrylamide solutions in that more precise sample injection and compaction is possible. Since sample shape is particularly significant in microscale separations since the size of the injected sample plug makes a greater relative contribution to the total fluorescence peak width and, hence, the overall separation resolution than in traditional macroscale systems. Finally, the UV-initiated chemistry offers the ability to directly control the progression of the polymerization reaction through appropriate modulation of the incident illumination. The rate of initiation, which is directly proportional to the incident UV intensity, strongly influences the reaction kinetics and resulting gel morphology (e.g., chain length, crosslinking density, etc.) (Okay, O., *Polymer* 35:796–807, 1994; Naghash, H. J. and O. Okay, *J. Appl. Polymer Sci.* 60:971–979, 1994). Hence, it is possible to tailor the pore structure of the crosslinked network, potentially allowing the sieving properties of the gel to be matched to the size-range of a particular sample to be separated. For example, a spatially varying pore structure can be created within a single gel by simply masking various sections of the separation channel so that they each experience a different amount of UV illumination.

V. Design of Electrodes

The main design parameters involved in the efficient design of electrode-defined sample compaction and injection systems are: the choice of the electrode material, the size (width) of the electrode, and the position of the electrodes.

The choice of the electrode material is defined by the ease of microfabrication of the material, the adhesion/release characteristics of the DNA at the electrode material and the nature of electrolytic effects at the electrodes. Platinum electrodes are the preferred choice of electrode material for electrophoretic separations. In addition, DNA adsorbs permanently to certain metals such as aluminum 9260 which necessitates the use of noble metals as electrode material. Without limiting the present invention to a particular type of electrode and since the electrodes used for sample compaction and electrophoretic separation were both fabricated in the same process step, platinum electrodes (with a titanium adhesion layer) were used in the present invention. We have observed excellent collection and release behavior of DNA in the presence of electric fields with these platinum electrodes. Although the present invention is not limited to any particular mechanism, it is believed that electrodes spanning the entire width of the channel force a uniform electric field distribution, even at close proximity to the sieving medium.

Experimental

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); g (grams); mg (milligrams); $\mu$g (micrograms); L (liters); ml (milliliters); $\mu$l (microliters); cm (centimeters); mm (millimeters); $\mu$m (micrometers); mn (nanometers); ° C. (degrees Centigrade)

EXAMPLE 1

Electrophoresis Procedure

Prior to electrophoresis runs, the microchannels (prepared as described above) were rinsed with acetone, isopropanol (IPA) and distilled/deionized water to remove particulate and organic matter. Following this clean, the channels were treated with RainX AntiFog solution (Blue Coral, Cleveland, Ohio) to promote uniform wetting on all channel surfaces by the gel reagents. *Photopolymerizable* polyacrylamide gels were prepared by using the commercial ReproGel™ (Amersham Pharmacia, Kalamazoo, Mich.) system (see, U.S. Pat. No. 5,873,991 to Göthe, incorporated herein by reference). The gel solution was prepared by mixing 10 $\mu$l of solution A (acrylamide stock solution) with 20 $\mu$l of solution B and was loaded into the entire channel network by placing a drop of premixed solution at one end of the separation channel. The device was masked in all sections except where polymerization was desired and exposed to a UVA illumination from a 40 watt mercury vapor bulb; after illumination, the unpolymerized solution was aspirated, and the arms of the channel network are rinsed with DI water and filled with a fluorescently labeled DNA sample.

Double stranded DNA ladders (100 bp and 20 bp at 100 ng/$\mu$L concentration) were purchased from Bio-Rad (Hercules, Calif.). The double stranded DNA ladders were labeled with YOYO-1 intercalating dye (Molecular Probes, Eugene, Oreg.) at a dye to DNA ratio of 1:10. A 0.5× Tris-borate-EDTA (TBE) solution (Bio-Rad, Calif.) was used as the running buffer solution. The migrating bands were detected using an Olympus SZX 12 fluorescence stereoscope and a cooled CCD camera (TEC 300; Michigan City, Ind.). The output of the camera was digitized using NIH Image 1.61. Applying an intermediate buffer run or "rinse" between DNA separation runs enhances reusability.

EXAMPLE 2

Photopolymerized Polyacrylamide Gels

Having selected the commercially available UV initiated ReproGel™ formulation, the gel casting process was greatly simplified. Two variations of the polymerization mixture were studied: ReproGel™ High Resolution, containing 8% (w/v) acrylamide/bisacrylamide monomers and 1× TBE buffer, and ReproGel™ Long Read, containing 7% (w/v) acrylamide/bisacrylamide monomers and 1.5× TBE buffer. The characteristically small dimensions of microfabricated separation channels demand that care be taken to preserve the integrity of the gel during the casting process by avoiding the introduction of impurities and eliminating bubble formation during the polymerization reaction. However, we found that reproducible high-resolution separations were achievable using the as-received reagents, without the need for additional purification and/or degassing.

Flat and uniform gel interfaces in the sample loading region could be achieved by partially filling the channel to the desired level with the monomer/crosslinker mixture, however the precise location of the interface exhibited a slight degree of variability due to normal shrinkage of the gel matrix during the course of the polymerization reaction. More precise placement of the gel interface was accomplished by first filling the entire channel with the prepolymer mixture and then masking the injection region with opaque tape (FIGS. 1*a*–*d*; (a) empty separation channel, (b) channel filled with monomer/crosslinker mixture, (c) channel sections masked for polymerization, (d) final polymerized gel). Upon exposure to UV illumination, polymerization only occurs in the unmasked portions of the channel, after which the unpolymerized reactants in the injection region can be easily removed prior to sample loading.

Using this procedure, we were able to routinely cast gels incorporating well-defined flat interfaces at precise locations within a microfabricated channel (FIGS. 1*e*, 1*f*; (e) photograph of typical gel interface (arrow denoted gel interface), (f) localization of gel interface in a complex microchannel network). A further benefit of photopolymerizable gel formulations is the ability to precisely position an electrophoresis column at any location within a complex microdevice. FIG. 1*f* shows an example of a gel segment with well-defined interfaces located within a larger channel network using the masking techniques described above. This strict localization of the gel interface was not easily obtained with traditional chemically polymerized gel formulations, and allows additional flexibility in the design of integrated DNA analysis systems.

EXAMPLE 3

Optimization Of Photopolymerization Time

Optimization of the polymerization protocol focused on adjusting UV intensity and polymerization time, both of which strongly affect the rate of initiation, with the aim of maximizing separation performance with minimal run-to-run variability. The Reproset™ UV illumination source (Amersham Pharmacia, Kalamazoo, Mich.), designed specifically for use with the ReproGel™ reagents, provided more consistent results than a lower-intensity UV lamp (UVP, San Gabriel, Calif.) and was used as provided in the manufacturers materials. Separation performance was evaluated by observing the migration of a fluorescently labeled 20 base pair molecular ladder (FIGS. 2a–d; samples were directly compacted at the gel interface by application of an electric field (E=10 V/cm) for 20 s. Separation was conducted at E=20 V/cm. Migration direction is left to right. Data shown corresponds to gel polymerization times of (a) 2, (b) 6, (c) 7 and (d) 8 minutes. The double bright and is the 200 bp fragment). Although reliable separations could be obtained after polymerization times as short as 2 minutes, we found that cure times of 6–7 minutes (ReproGel™ High Resolution) or 8–10 minutes (ReproGel™ Long Read) produced optimal results (i.e., allowed the most number of bands to be resolved). These polymerization times are slightly shorter than the 10–12 minutes recommended by the manufacturer, most likely due to the considerably reduced thickness of the separation channel and surrounding glass wafer relative to the dimensions of standard sequencing gel cassettes. In addition, the gels in the present study were used in a 'native' or non-denaturing mode since the separations were performed at room temperature and this may account for the shorter optimum polymerization times.

Significant band curvature is observed while using the photopolymerized polyacrylamide gel system for separations in microchannels. From further observation, it appears that in some cases the acrylamide along the channel edges may not have completely polymerized (resulting in a rapid migration along the edge, or frowning). It was also possible that the trapezoidal channel profile (produced as a result of the isotropic glass etch) could result in curved bands. Other channel depths, etch techniques, and/or glass formulations may be used to produce rectangular or smooth curved side-walls. The use of covalent binding agents such as BindSilane™ (Amersham Pharmacia, Kalamazoo) or other surface treatments may also alleviate this problem.

Alternatively, microfabrication offers the possibility of fabricating on-chip fluorescence detectors. Fabrication of 10 µm wide photodetectors and reported the on-chip detection of migrating DNA band has been demonstrated (Burns, M. A., et ai., *Science* 282:484–487, 1998; Brahmasandra, S. N., et al., *Proceedings of the SPIE* Santa Clara, Calif., pp.2420251, 1998). By microfabricating on-chip photodetectors spanning only the central portion of the channel to selectively image a section of the channel or by fabricating curved photodetectors to mimic the curvature of the bands, as contemplated in the present invention, the complications of detecting curved bands are avoided. Band curvature was also significantly reduced when the separations were carried out at an elevated temperature (45–55°) (Bousse, L., et al., *Proceedings of the µ/TAS'98 workshop*, Banff, Canada, pp.271–275, 1998). Although the present invention is not limited to any particular mechanism, this observation indicates that the temperature of the gel plays an important role in influencing the shape of resulting bands. In all our experiments, however, the band curvature did not significantly affect the resolution of separation due to spatially selective imaging.

EXAMPLE 4

Microseparations Using Photopolymerized Polyacrylamide

The first step in electrophoresis after loading the sieving matrix is sample injection. Sample injection in a non-crosslinked sieving media is normally executed electrokinetically using a cross channel with the sample channel perpendicular to the separation channel. For crosslinked media, electrophoretic injection was used. In this technique, a short pulse of a relatively high electric field (10 V/cm for 10 to 20 seconds) was applied between the ends of the separation channel, resulting in compaction of the sample at the gel interface as a consequence of the discontinuity in electrophoretic mobilities inside and outside the gel. After compaction, the field was switched off and the injection ports are flushed with buffer solution. Alternatively, electric fields can be used to achieve an electronic flush to prevent excess sample from entering the separation matrix. Finally, the field was switched back on and increased to the level used during the actual separation. However, the level of sample compaction attainable using this technique faces a practical limitation imposed by the tradeoff between increased focusing at longer compaction times, and a reduction in separation resolution due to continuous migration of DNA fragments into the gel during compaction.

Figure 3A:
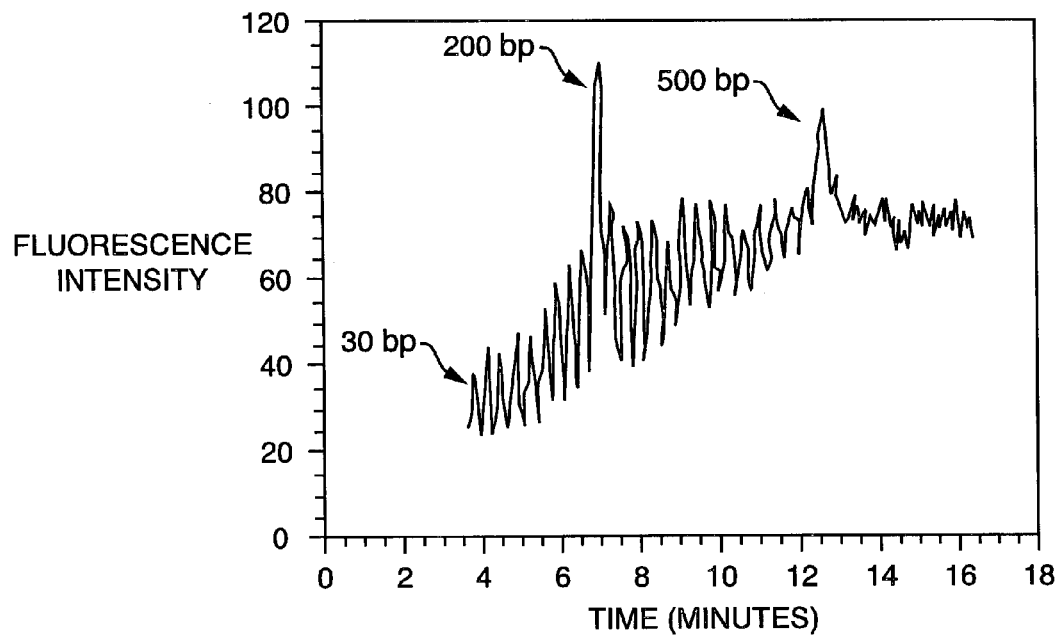
FIGS. 3a and 3b show separations of YOYO-1 labeled double stranded DNA in a photopolymerized polyacrylamide gel. Intensity data are extracted directly from a video image sequence by averaging over a 30 $\mu$m square "detection" area (see FIG. 4). (a) 20 bp ladder DNA: detector located 0.4 cm downstream from gel interface (E=20 V/cm) and (b) OX174/Hae III digest: detector located 0.18 cm downstream from the gel interface (E=16 V/cm). The asterisk (*) denotes fragments known to exhibit anomalous mobility in polyacrylamide gels.
Figure 3B:
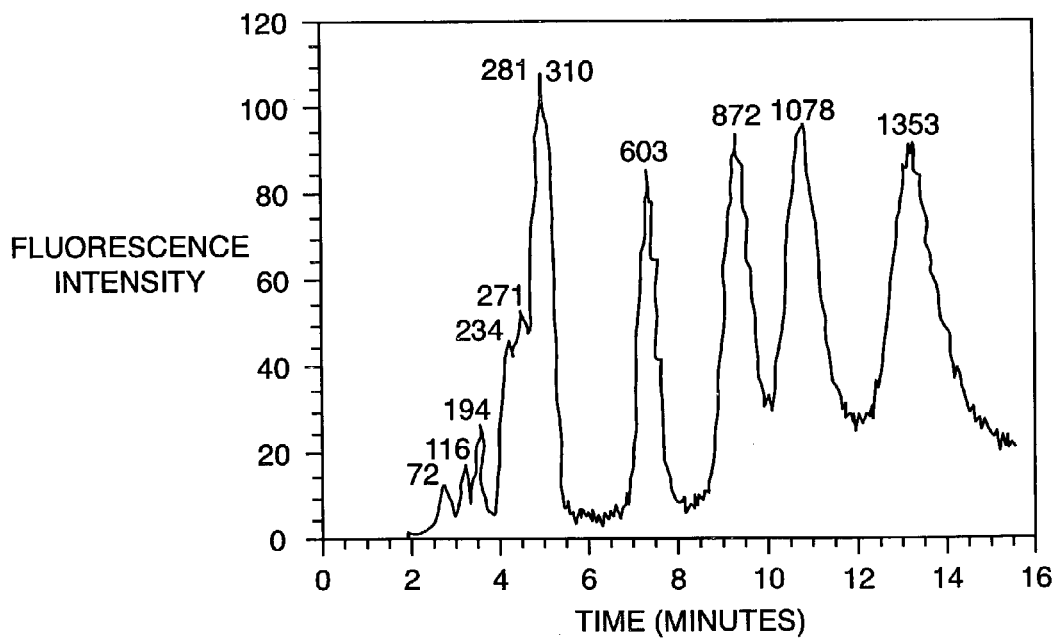

FIG. 3a shows a plot of fluorescence intensity as a function of time during separation of a YOYO-1 labeled 20 base pair ladder using the ReproGel™ High Resolution formulation. Intensity data are extracted directly from a video image sequence by averaging over a 30 µm square "detection" area (see FIG. 4). The detector was located 0.4 cm downstream from gel interface (E=20 V/cm ). Sample compaction was accomplished using electrophoretic injection for 20 seconds at an electric field strength of 9 V/cm. Excess sample was flushed and electrophoresis was performed at an electric field 20 V/cm. Intensity data are extracted directly from a video image sequence by averaging over a 30 µm square "detection" area located along the channel centerline at a distance of 0.4 cm downstream from the gel interface. These data (FIG. 3a) show that photopolymerized polyacrylamide gels allow high resolution separations to be performed in short distances at low electric field strengths, making them well suited for use in microfabricated systems. FIG. 3b shows fluorescence intensity as a function of time for separation of a ⊖X174/Hac III digest using the ReproGel™ Long Read formulation. The detector was located 0.18 cm downstream from the gel interface (E=16 V/cm). The asterisk (*) denotes fragments known to exhibit anomalous mobility in polyacrylamide gels. These data, collected at a distance of only 1.8 mm downstream from the gel interface, further demonstrate the utility of these photopolymerized gel formulations in micro-electrophoresis systems.

EXAMPLE 5

Electrode Defined Sample Injection

The resolution obtained in microfabricated separation systems is defined predominantly by two factors: the selectivity of the sieving medium and the total peak broadening. The total sample band broadening depends on diffusion/dispersion, the size of the injected sample plug. Therefore, separation in a microchannel could be dominated by diffusion/dispersion effects or be limited by the size of the injected plug. However, in short microfabricated channels, it is likely that the separation is influenced very strongly by the size of the injected plug size, especially at low dispersion coefficient values (Washizu, et al., *Conference on Solid State Sensors and Actuators (Transducers '97)*, Chicago, Ill., pp.473–476, 1997). Consequently, the present invention provides injection techniques capable of delivering well-define, small sample injection plugs to the sieving matrix.

Figure 4A:
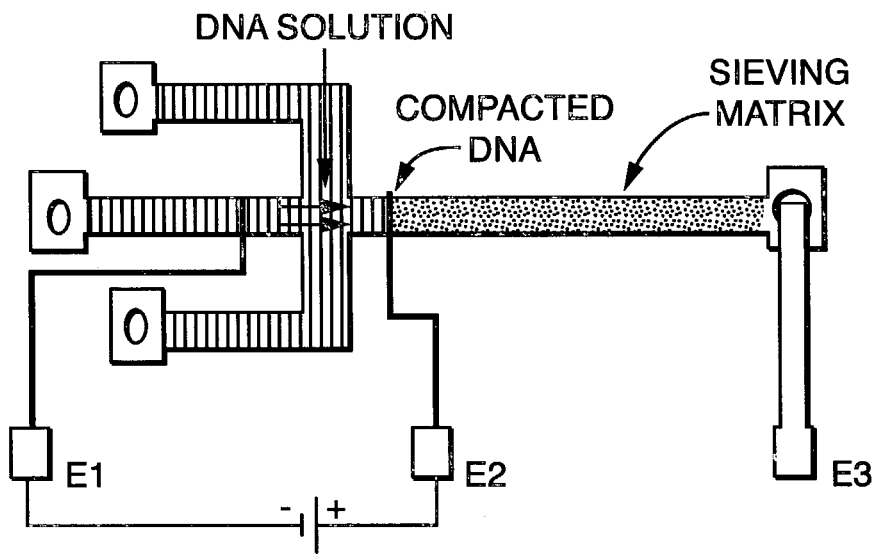
FIGS. 4a and 4b show sample compaction, definition and release using on-chip electrodes. (a) Negatively charged DNA molecules are compacted by applying a low positive potential to a thin electrode (Pt) of definite width. (b) Sample is released by switching the polarity of the electrode and injected onto a separation matrix.
Figure 4B:
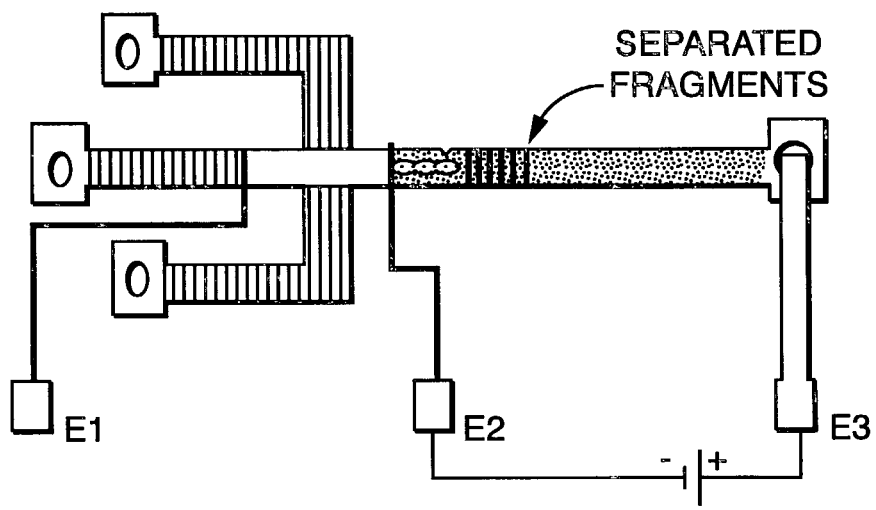

The present invention provides the use of microelectrodes to define the size, shape, and amount of the sample injected to a separation channel. The fundamental idea is presented in FIG. 4. An electric field is initially applied between microelectrodes E1 and E2. FIG. 4a shows the negatively charged DNA molecules are compacted by applying a low positive potential to a thin electrode (Pt) of definite width. The DNA migrates towards and collects at the positively changed electrode E2 that is positioned just outside of the gel interface. This field can be applied for a specified time or until sufficient sample has accumulated at E2. The electric field was then switched to a different pair of electrodes (FIG. 4b) spanning the gel (E2 and E3). FIG. 4B shows the sample is released by switching the polarity of the electrode and injected onto a separation matrix. Since E2 is no longer at a positive potential, the DNA compacted at this electrode was released and injected onto the separation channel as a well-defined plug.

The amount of sample collected was defined by the electric field strength and time of sample compaction. The size and shape of the sample plug was defined by the size and shape of the electrode. Using this technique sample plug widths of 50 microns or less have been routinely achieved. The width of the sample plug was further reduced as a consequence of additional compaction at the gel interface after the sample is run into the gel. Hence, this novel loading scheme both increases the concentration of the sample to be separated and significantly reduces degradation in separation resolution due to the size of the injected sample plug, a quantity of increased relative importance in ultra-short systems. Such an approach has the potential of offering a simple and efficient method of simultaneous sample injection and compaction in microdevices using extremely low voltages.

EXAMPLE 6

Design Of Electrodes

Figure 5:
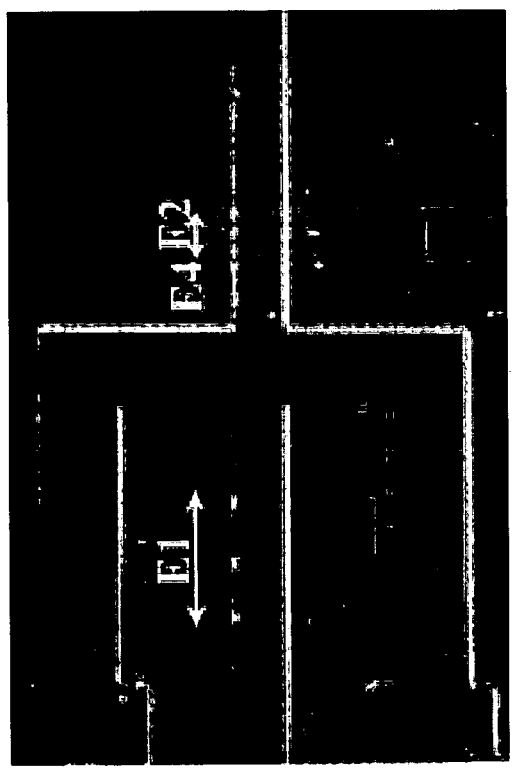
FIGS. 5a and 5b show a close up of the electrode arrangements in a microfabricated sample injection and separation system. (a) 50 $\mu$m thin electrodes (E1, E2) are used for sample compaction and separation. (b) A thick electrode (E4) is introduced to allow the use of higher voltages during the sample release and separation phase. (c), (d) Schematic of operation of electrode-defined sample compaction, release and subsequent separation for the electrode system shown in (b).
Figure 5:
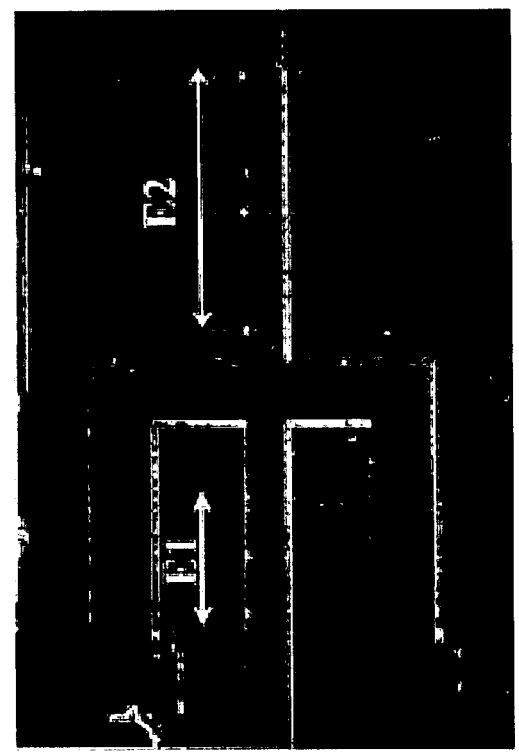

The present invention contemplates microfabricated separation systems with several different electrode arrangements, two such arrangements are shown in FIG. 5. The electrodes E1 and E2 were fabricated in sets of three to provide flexibility in positioning the channel and/or gel interface. The 50 $\mu$m thin electrodes (E1, E2) are used for sample compaction and separation. While the design achieved excellent compaction and release of DNA using the electrode arrangement shown in FIG. 5a, the subsequent electrophoresis was limited to low voltages (<15 V) due to bubbling at electrode E2. Upon release and injection of the sample plug onto the gel matrix, an additional flushing step was necessary to remove excess sample and to perform the separation at higher voltages using electrodes located at the two extremities of the device.

Figure 5C:
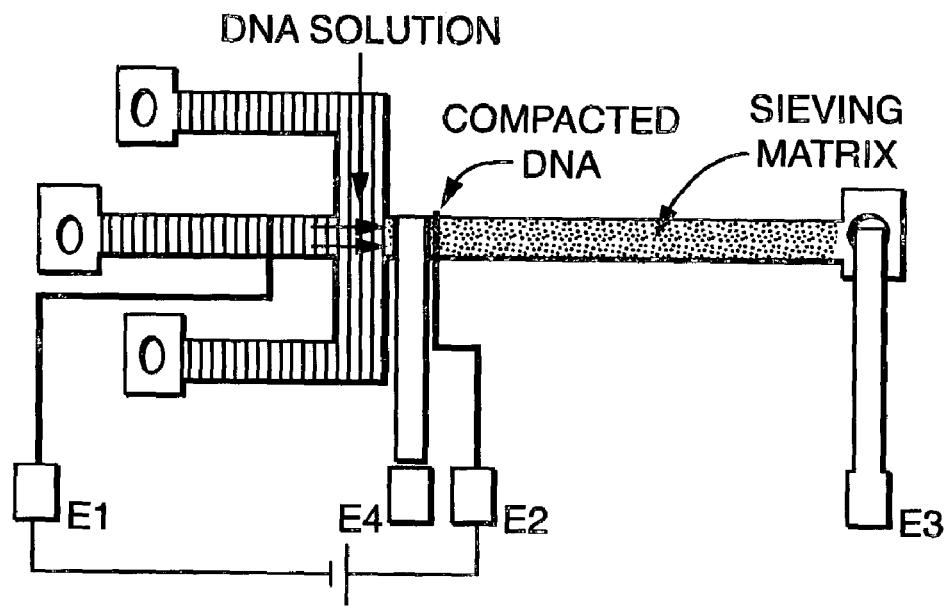
Figure 5D:
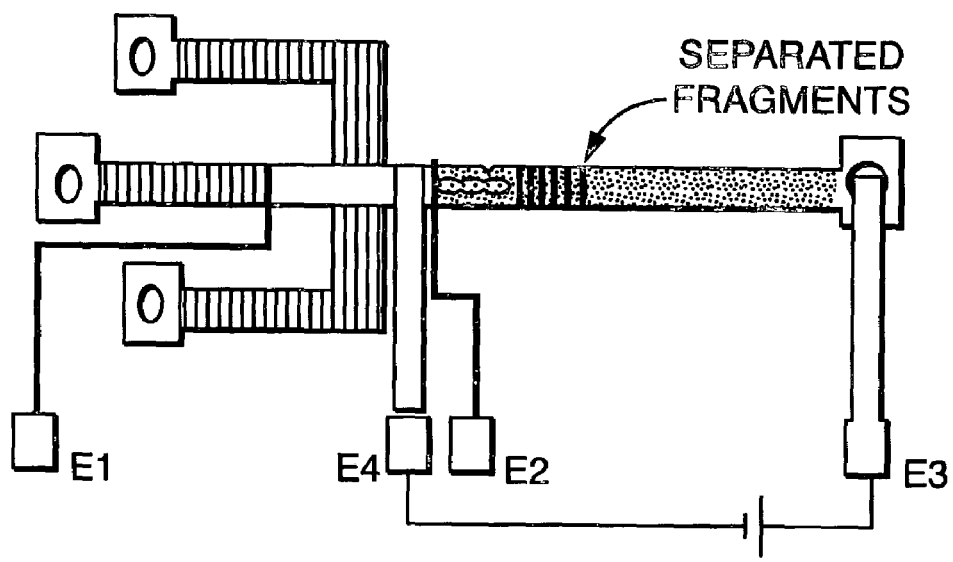

In an attempt to avoid this additional step, the device shown in FIG. 5b was fabricated. In this device, a new electrode (E4) was introduced to serve as the cathode during the separation process. The thick electrode (E4) was introduced to allow the use of higher voltages during the sample release and separation phase. A low voltage of 2.0 V was applied between electrodes E1 and E2 and the sample was compacted at electrode E2 (FIG. 5c) for ~30 seconds. FIGS. 5c and 5d show a schematic of operation of electrode-defined sample compaction, release and subsequent separation for the electrode system shown in (b). The field was then switched to two electrodes spanning the gel (E3, E4), and the sample was injected into the sieving matrix as a well-defined rectangular plug (FIG. 5d). The introduction of this wider electrode allowed higher voltages (~70 V) to be safely applied, without generation of bubbles during the separation step.

Although the present invention is not limited to any particular mechanism, it is believed that the phenomenon of bubbling of microelectrodes is governed by equilibrium between the rate of gas evolution at the microelectrodes and the rate of gas re-dissolution in the buffer. Gas evolution at the microelectrodes is initiated at very low voltages (Heller, M., et al., *Electrophoresis* 21:157–164, 2000). However, the evolved gas can either re-dissolve into solution or manifest itself as a bubble. For a given voltage and electrolyte conditions, a thinner electrode is likely to have a higher flux (mass per unit time per unit area) of gas evolution than a wider electrode. Consequently, the rate of gas evolution at the thinner electrode (at high voltages) is expected to be much higher than the rate of dissolution leading to the generation of bubbles. The wider electrode offers a larger surface for mass transfer (and hence gas dissolution) and consequently bubbling is avoided even at high gas evolution rates.

EXAMPLE 7

Sample Compaction

Sample compaction experiments were performed using devices with the electrode arrangement shown in FIG. 5b. Sample compaction at a 50 $\mu$m thin electrode (anode) was studied as a function of the separation length between the cathode and the anode (i.e., electric field strength). The rate and level of sample compaction achievable using the electroinjection procedure was estimated by monitoring the rise in intensity of a fluorescently labeled DNA sample (100 bp ladder dsDNA labeled with YOYO-1) at the capture electrode.

Figure 6:
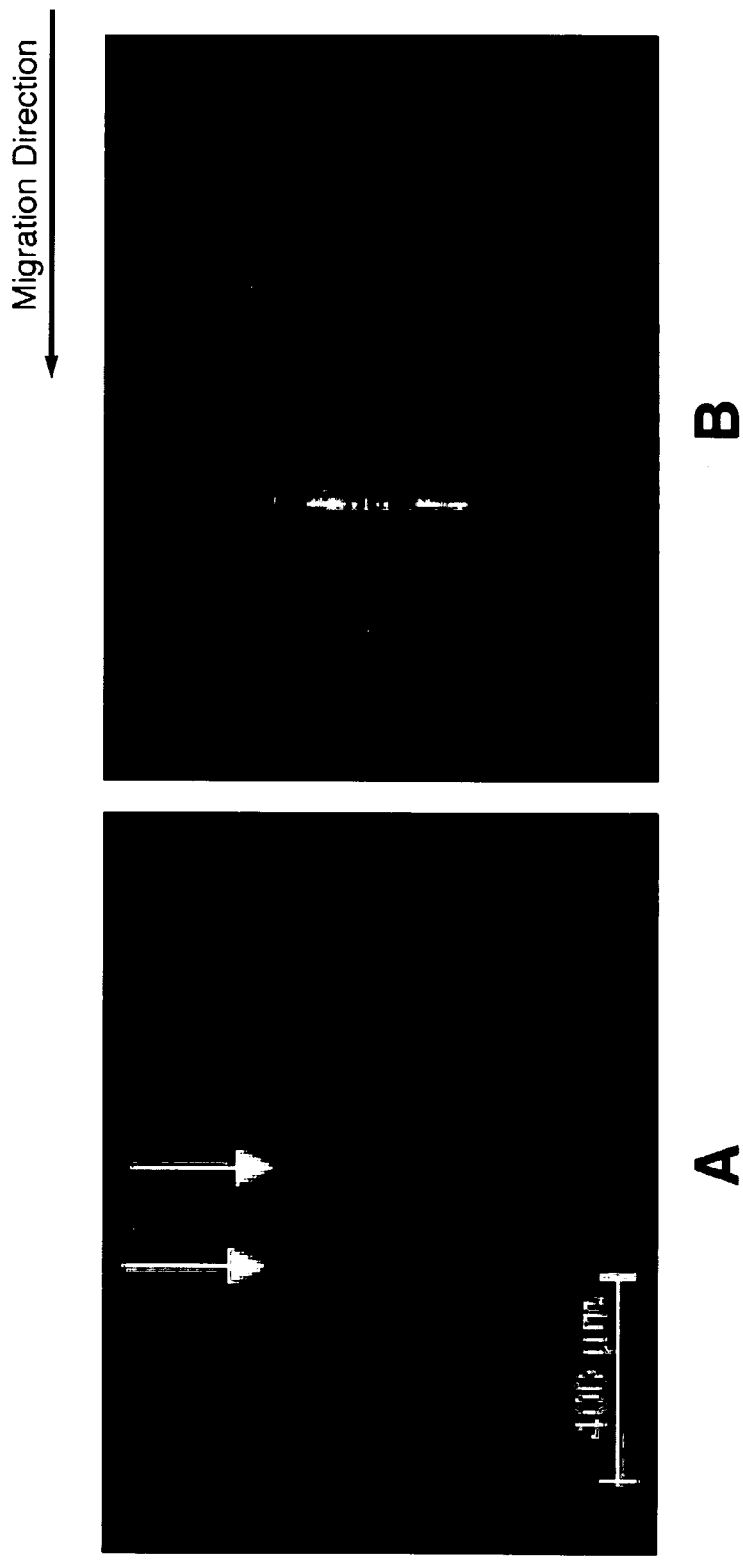
FIGS. 6a, 6b, 6c, 6d, 6e and 6f show sample (fluorescently labeled 100 bp ladder DNA at 100 ng/$\mu$L concentration) compaction at anode as a function of distance between the two compacting electrodes. Distance between the electrode was (a), (b) 250 $\mu$m (c), (d) 700 $\mu$m (e), (f) 1600 $\mu$m. Arrows point to the set of compacting electrodes used except in (c) where the cathode is out of range of view.
Figure 6:
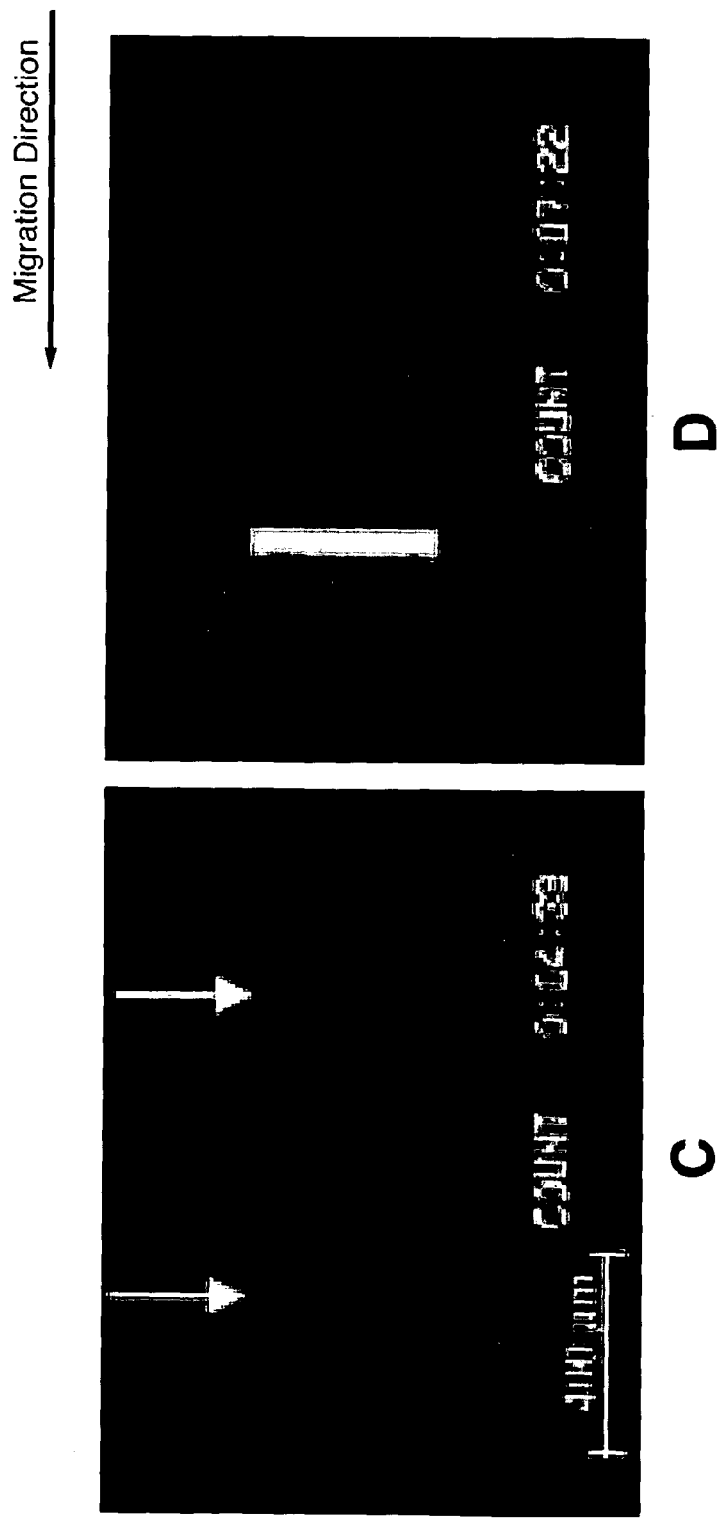
Figure 6:
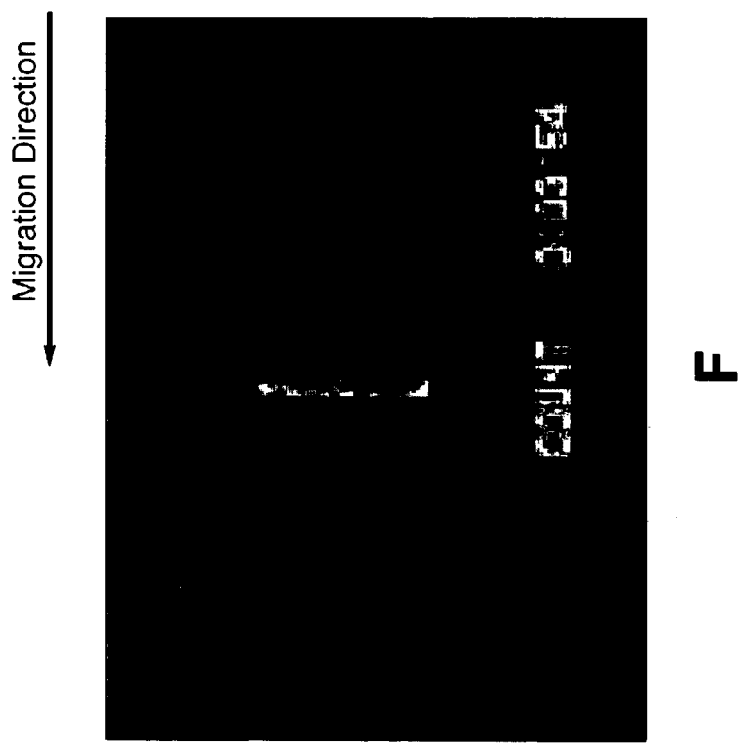
Figure 6:
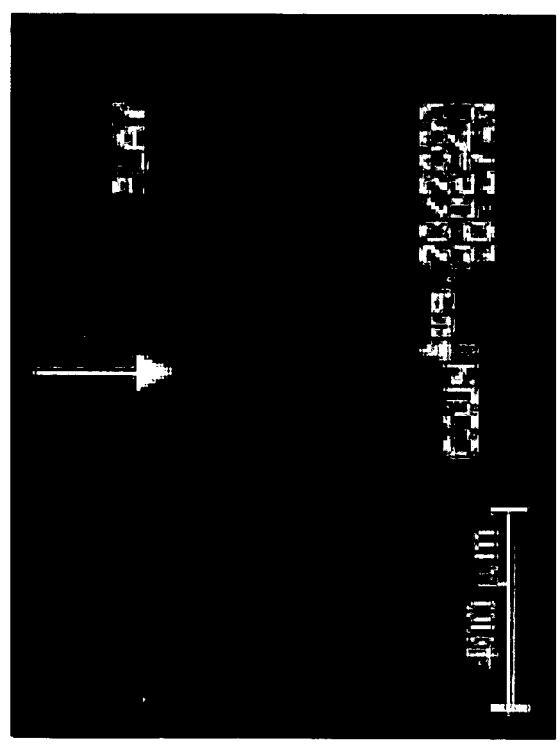

The distance between the two electrodes defines both the total sample available for the compaction, and the electric field between the two electrodes. Typically a voltage of 2.0 V was applied between two electrodes separated by 250–1600 $\mu$m resulting in electric field strengths of ~12–80 V/cm. At higher voltages (>2 V), the electrolytic effects appear to adversely affect the finding of DNA to the electrode. The results of sample compaction studies at three representative electric fields (electrodes separated by three different distances) are shown in FIGS. 6. In FIG. 6, a constant voltage of 2.0 V was used resulting in different electric field strengths. Distance between the electrode was (a), (b) 250 $\mu$m (c), (d) 700 $\mu$m (e), (f) 1600 $\mu$m. Arrows point to the set of compacting electrodes used except in (c) where the cathode is out of range of view. Compaction of fluorescently tagged DNA molecules is apparent from the increase in fluorescence intensity at the compacting electrode. We have observed significantly enhanced level of sample concentration at the compacting electrode using this method of injection.

Figure 7A:
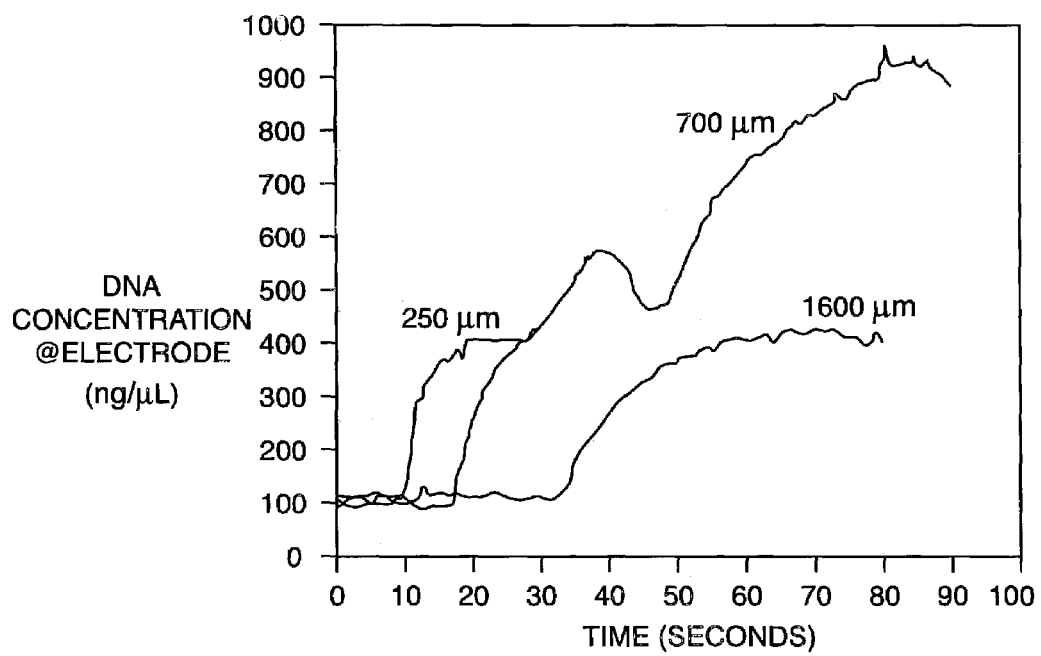
FIGS. 7a and 7b show (a) compaction of DNA at a microelectrode and, (b) Extent of concentration enhancement ($C_{final}/C_{initial}$) as a function of the distance between the two electrodes.

In FIG. 7a, the transient rise in DNA concentration, upon application of the electric field, at the compacting electrode using two 50 $\mu$m wide electrodes separated by either 250, 700 or 1600 $\mu$m, has been plotted. The rate of compaction appears to decrease with decreasing electric field strengths (electrodes separated by larger distances) as evident from the decreasing slopes of the three curves, and the concentration of DNA at the electrode appears to reach a constant level upon continued application of the electric field. When the electrodes were separated by 700 $\mu$m a dip in the transient sample compaction at the electrode was observed.

Visually, it appeared that, after an initial compaction period, the compacting DNA was swept away from the electrode. However, upon continued application of the electric field, further sample compaction was achieved.

Figure 7B:
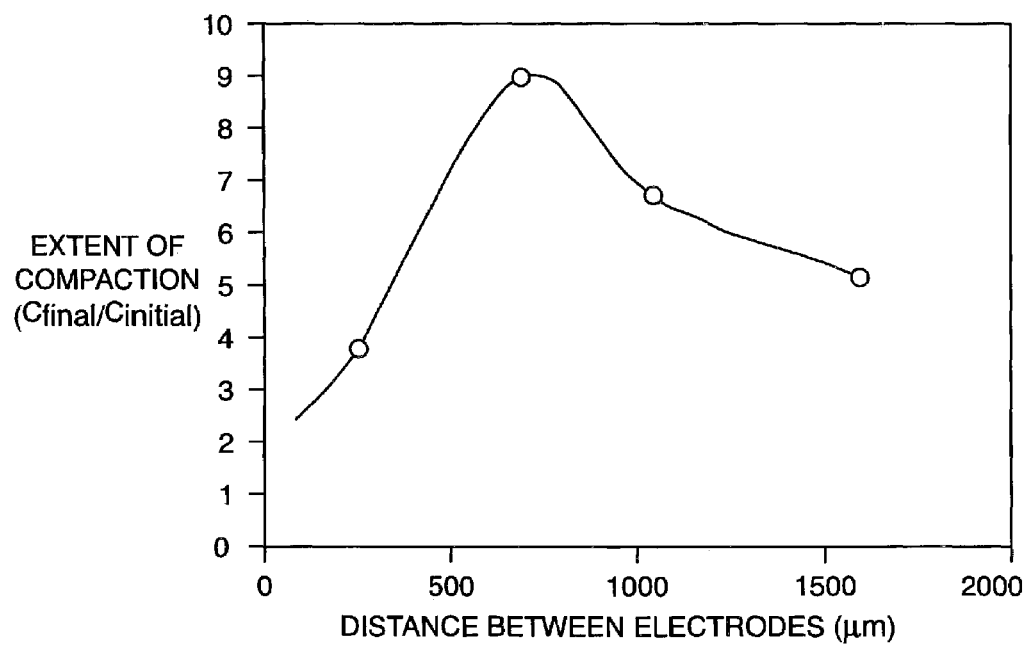

In FIG. 7b, the steady state level of enhancement obtained is plotted as a function of the separation between the two compacting electrodes. The magnitude of enhancement initially increases with increasing separation between the electrodes, appears to reach an optimum, and decreases at larger separation between the two electrodes. This behavior can be attributed to the interplay of two factors—the sample volume available for compaction and the electric field strength between the two electrodes. When the two electrodes are spaced close together, the high electric field strength results in efficient sample compaction. However, due to the low sample volume available for compaction, the final enhancement of sample concentration is low. At larger separation between the electrodes there is a large sample volume available for compaction, but the low electric field strengths result in low efficiency of compaction. This results in a relatively low level of sample enhancement. Consequently, it was noticed that similar enhancement of concentration (~4×) is obtained when electrodes are separated by either 250 $\mu$m or 1600 $\mu$m and a separation of 700 $\mu$m between the two electrodes appears to be the optimal electrode separation for this voltage. Although the present invention is not limited to any particular mechanism, the measured levels of concentration enhancement at the electrode could be influenced by fluorescence shielding/quenching as a result of the vertical distribution of the sample at the electrode.

EXAMPLE 8

Integrated Compaction And Separation

Upon testing the sample compaction and release characteristics of the separation systems incorporating microelectrodes, the feasibility of using the electrode defined injection scheme for electrophoretic separations was tested. A device, with the electrode arrangement shown in FIG. 5b, was assembled and operated as shown in FIGS. 5c, d.

Figure 8:
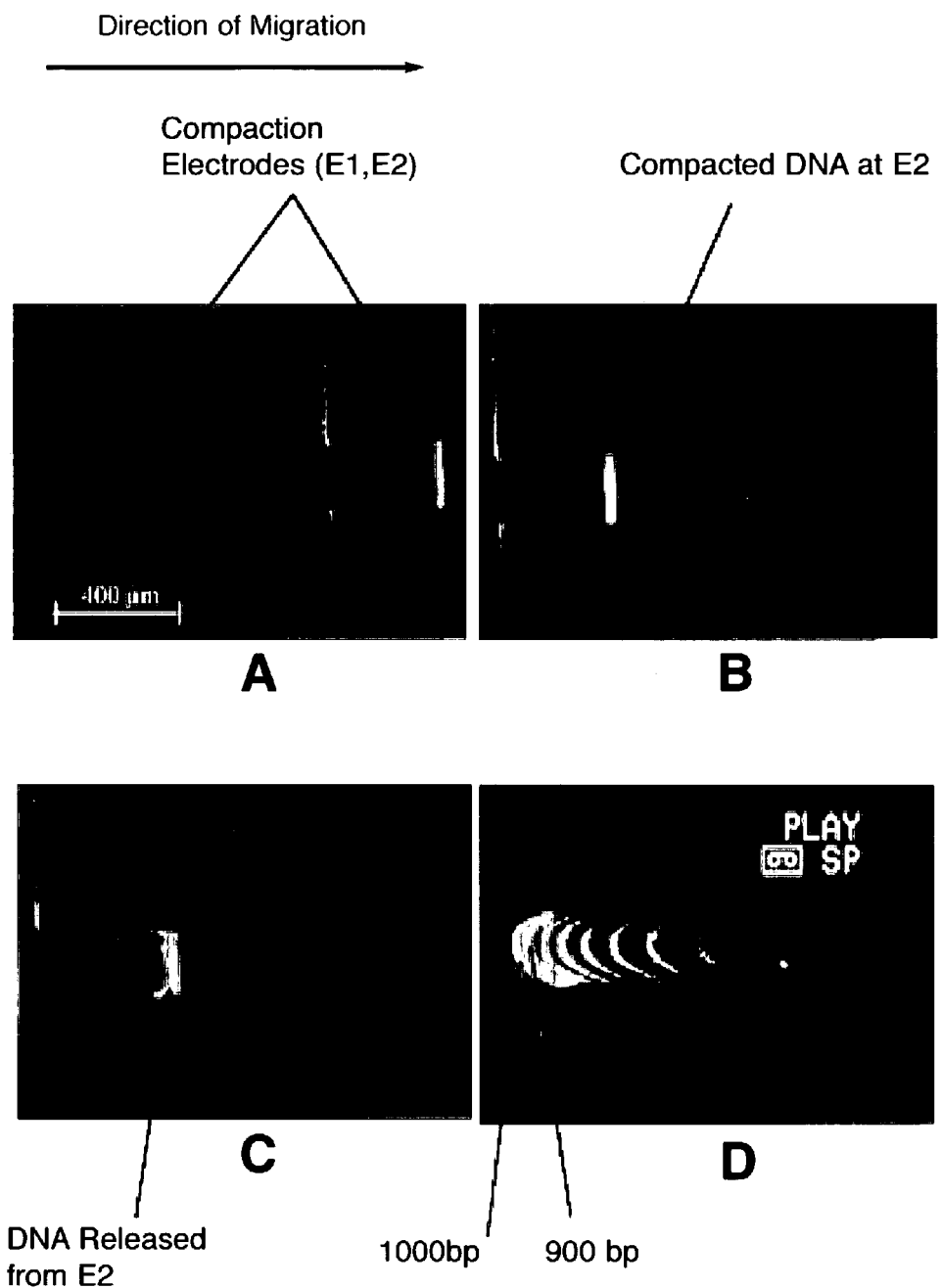
FIGS. 8a, 8b, 8c and 8d show a video sequence depicting the feasibility of microseparations using electrode defined sample compaction/injection and photopolymerized polyacrylamide gel sieving matrix. (a), (b) A fluorescently labeled 100 bp ladder DNA was compacted at a 50 $\mu$m electrode b applying an electric field of ~12 V/cm between E1 and E2. (c) Compacted sample was released by switching the electric field to two electrodes spanning the gel matrix. (d) Complete resolution of all fragments was achieved in a separation length of 0.18 cm in less that 15 minutes. Separation was conducted at E=20 V/cm; migration direction is left to right.

A 100 bp dsDNA ladder was separated using this technique of sample injection in a photopolymerized polyacrylamide gel sieving matrix. The sample was electro-injected for ~30 seconds resulting in ~5× increase in sample concentration at the electrode. The compacted sample was released and injected onto the separation matrix where it underwent further compaction due to the inherent sample stacking that occurs at the gel interface. Separation was continued at a field strength of 20 V/cm. No bubbling was observed at the cathode and all the fragments were resolved in a separation length ~1.8 mm. A sequence of video images from this separation are shown in FIGS. 8 (a–d). FIGS. 8a and 8b shows fluorescently labeled 100 bp ladder DNA was compacted at a 50 $\mu$m electrode b applying an electric field of ~12 V/cm between E1 and E2. FIG. 8c shows a compacted sample was released by switching the electric field to two electrodes spanning the gel matrix. FIG. 8d shows a complete resolution of all fragments was achieved in a separation length of 0.18 cm in less that 15 minutes. Separation was conducted at E=20 V/cm; migration direction is left to right.

Figure 9A:
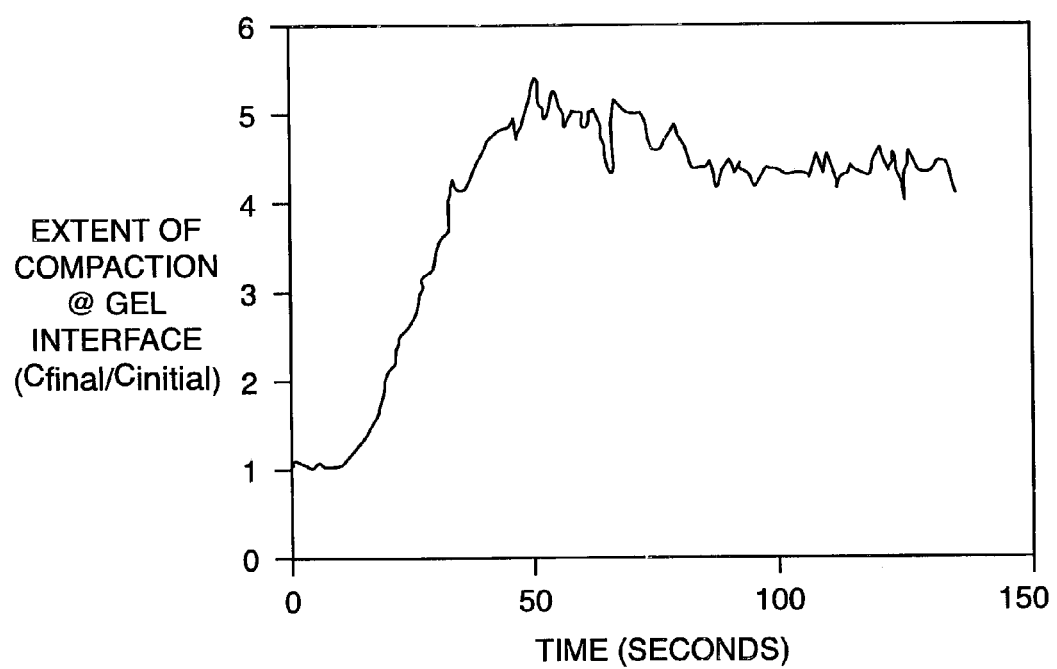
FIGS. 9a, 9b and 9c show separation using simple electrophoretic injection scheme. (a) Extent of sample compaction at the gel interface obtained using the electrophoretic injection techniques. (b), (c), (d) Sequence of video stills showing compaction at the gel interface. (c) At a downstream distance of approximately 2 mm, there is insufficient resolution to distinguish separated fragments greater than 500 base pair in length.
Figure 9:
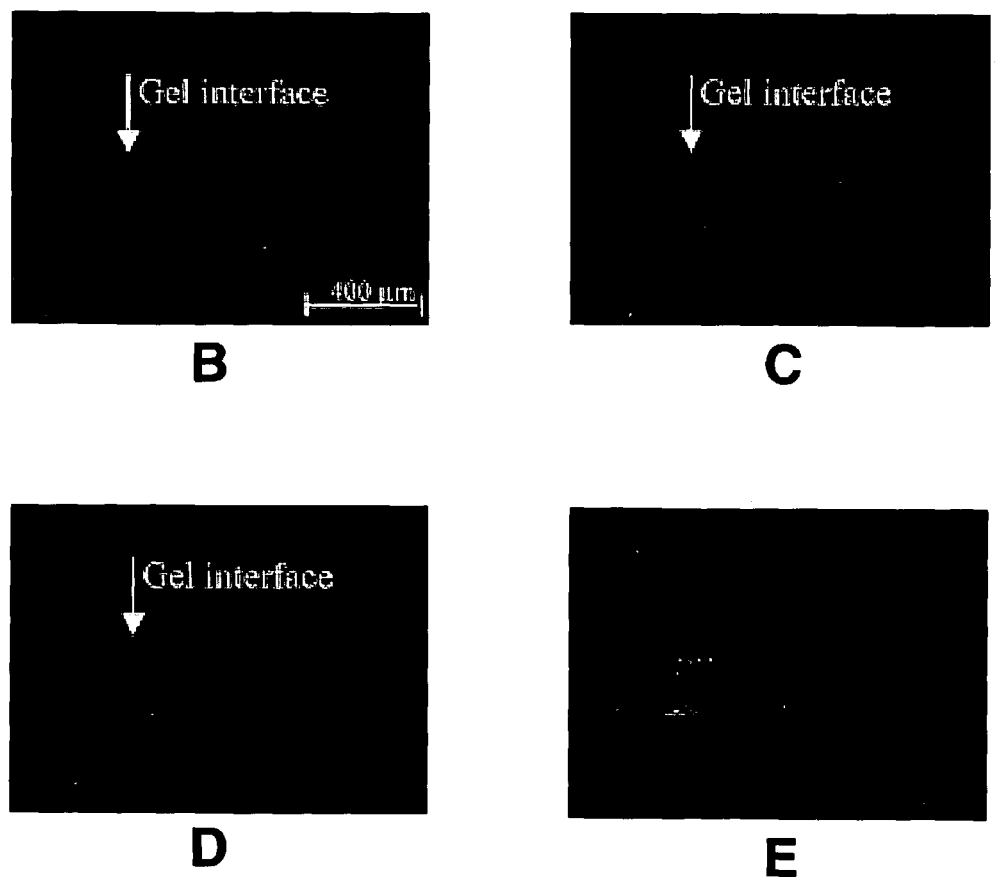

The separation resolution obtained using an electrode defined sample compaction was compared with that obtained using a simple cross injection scheme mentioned earlier (Example 5). Again, a fluorescently labeled 100 bp dsDNA ladder was used as the sample; sample compaction, and separation resolution using the cross injection scheme were studied. Following an initial increase, the DNA concentration at the gel interface quickly reaches a plateau when observed within a fixed window located at the gel interface (FIG. 9a). This plateau arises as a consequence of a steady state between the rate of compaction at the gel interface and the rate of DNA migration into the gel. For a consistent comparison of the two injection schemes (electrode and cross injection), the sample at the gel interfaces were compacted to the same level on concentration obtained using the electro-injection technique i.e., we compacted the sample at the gel interface until a 5× sample compaction was observed at the gel interface (as measured by the increase in fluorescence intensity).

The captured video images (FIGS. 9b–d) show that sample compaction occurring at the gel-buffer interface. It appears that the sample compaction at the gel interface can be characterized in terms of two distinct regions: a primary compaction region where the most of the increase in sample concentration is localized (FIG. 9c; at a downstream distance of approximately 2 mm, there is insufficient resolution to distinguish separated fragments greater than 500 base pair in length), and a secondary migration region where DNA begins to enter the gel under the influence of the relatively high electric field (FIG. 9d). Image analysis reveals that after two minutes of electrophoretic injection, the width of the primary compaction region grows to approximately 200 microns while the secondary migration region extends an additional 275 microns into the gel. Hence, the 5× increase in concentration is obtained at the expense of a continuous increase in the sample plug width. At a downstream distance of approximately 2 mm, there is insufficient resolution to distinguish separated fragments greater than 500 base pairs in length (FIG. 9c). However, complete resolution of all the bands could have been achieved either by using a longer separation length, or by using a shorter injection time.

Figure 10:
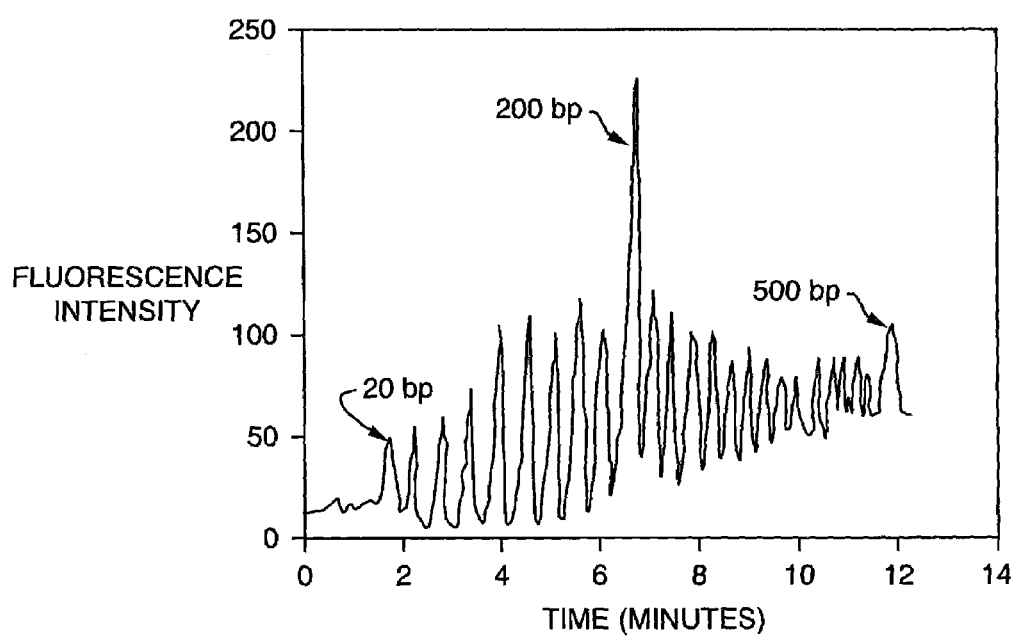
FIG. 10 shows separation using electrode-defined sample injection and photopolymerized polyacrylamide gels.

Once the feasibility (and advantage) of separations using electrode defined sample injection was established, the resolving power of this separation system by attempting the high-resolution separation dsDNA using the same injection strategy was investigated. Polyacrylamide gel was photopolymerized as before, and a 20 bp dsDNA ladder sample fluorescently labeled with YOYO-1 intercalating dye was introduced into the arms of the microchannel network. The DNA sample was compacted onto a 50 $\mu$m thin electrode for ~60 seconds. The compacted sample plug was released and injected onto the gel matrix by switching the electric field. Intensity data are extracted directly from a video image sequence by averaging over a 30 $\mu$m square "detection" area 0.32 cm downstream of the gel interface. Complete separation of a 20 bp ladder is achieved in ~12 minutes and at a shorter separation distance that without electroinjection (see FIG. 5). Complete resolution of all bands up to 50 bases was achieved in ~0.3 cm (FIG. 10), less than the 0.45 cm separation distance required to achieve comparable resolution using the simple electrophoretic injection schemes (FIG. 3a). Hence, this improved injection scheme has allowed the separation distance to be reduced by nearly 30% without any loss of resolution.

EXAMPLE 9

As shown in FIGS. 11(a–c), temperature sensors are located directly beneath the electrophoresis channel in order to provide an accurate reading of the temperature inside the gel. The RTDs (resistance temperature detectors) were located directly beneath the electrophoresis channel in order to provide the most accurate reading of the temperature inside the gel. The heater modules, on the other hand, were positioned to the side of the separation channel in a staggered arrangement in order to minimize unwanted reflection from the illumination source. Calibration was performed by placing each device in an oven and monitoring the resistance of the sensors at three different temperatures in the vicinity of 50° C. The oven was allowed to equilibrate for at least 30 min at each temperature prior to measuring resistances. On-chip temperature control was achieved by resistive heating in response to a potential applied to the heater elements. The heaters consume approximately 300 mW of power in order to maintain a temperature of about 50° C. inside the electrophoresis channel. A steady state temperature was typically reached in 3–5 mins, and active control of the heaters was necessary to maintain a constant operating temperature over the timescale of the experiments owing to the thermal equilibration between the device assembly and the surrounding air. All separation runs were conducted at a standard denaturing temperature of 50° C.

From the foregoing, it is clear that the present invention provides methods and materials for the production and utilization of a novel, small-scale, electrophoretic separation system based on a) photodefined polyacrylamide gels and b) electrode-defined sample injection giving superior resolution at a reduced cost and in less time.

What is claimed is:

1. A method comprising:
   (a) providing;
      (I) a microelectrophoresis device comprising a polymer deposited in a electrophoresis channel;
      (ii) first and second microelectrodes, wherein said second microelectrode is located approximately at the surface of said polymer and said first microelectrode is located approximately in a loading channel; and
      (iii) a sample;
   (b) introducing the sample to said loading channel to produce a loaded channel;
   (c) applying a negative charge to said first microelectrode and applying a positive charge to said second microelectrode to concentrate said sample at said second microelectrode, forming a compacted sample injection plug; and
   (d) releasing said compacted sample on to said polymer.

2. The method of claim 1, wherein said first microelectrode is located 250 to 1600 $\mu$m from said second microelectrode.

3. The device of claim 1, wherein said polymer is a crosslinked gel.

4. The device of claim 1, wherein a polymer is deposited in said one or more loading channels.

5. The device of claim 1, wherein said loading channel comprises glass, silicon or plastic.

6. The method of claim 1, wherein said polymer has diffusion and displacement coefficients, and the diffusion and displacement coefficients of said polymer are controlled by varying an intensity of a UV radiation.

7. The method of claim 1, wherein said polymer has a concentration between about 2 and 15% (w/v) in buffer.

8. The method of claim 1, wherein the sieving performance of said polymer is controlled by the temperature of said polymer at the time said negative and positive charges are applied to said first and second microelectrodes.

9. A method, comprising:
   a) providing a sample and a device, wherein said device comprises
      i) a housing;
      ii) one or more channels etched into said housing;
      iii) a separation matrix deposited in said one or more channels said matrix comprising an interface; and
      iv) a first microelectrode pair and a second microelectrode pair;
   b) applying an electric field with said first microelectrode pair to compact said sample at said interface; and
   c) applying an electric field with said second microelectrode pair to release said sample and inject said compact sample into said separation matrix.

10. The method of claim 9, wherein said sample comprises negatively charged DNA.

* * * * *